(12) United States Patent
Sakai

(10) Patent No.: US 11,331,222 B2
(45) Date of Patent: May 17, 2022

(54) METHOD FOR FORMING ELASTIC FILM STRETCHABLE STRUCTURE, AND ABSORBENT ARTICLE

(71) Applicant: Daio Paper Corporation, Ehime (JP)

(72) Inventor: Syunsuke Sakai, Tochigi (JP)

(73) Assignee: Daio Paper Corporation, Ehime (JP)

( * ) Notice: Subject to any disclaimer, the term of this patent is extended or adjusted under 35 U.S.C. 154(b) by 796 days.

(21) Appl. No.: 16/082,798

(22) PCT Filed: Feb. 24, 2017

(86) PCT No.: PCT/JP2017/006999
§ 371 (c)(1),
(2) Date: Sep. 6, 2018

(87) PCT Pub. No.: WO2017/163754
PCT Pub. Date: Sep. 28, 2017

(65) Prior Publication Data
US 2019/0083323 A1 Mar. 21, 2019

(30) Foreign Application Priority Data
Mar. 24, 2016 (JP) .............................. JP2016-060316

(51) Int. Cl.
| | |
|---|---|
| *A61F 13/15* | (2006.01) |
| *A61F 13/49* | (2006.01) |
| *A61F 13/496* | (2006.01) |
| *B32B 37/04* | (2006.01) |
| *B32B 37/14* | (2006.01) |
| *B29C 65/08* | (2006.01) |
| *B32B 5/02* | (2006.01) |
| *B32B 5/08* | (2006.01) |
| *B32B 27/08* | (2006.01) |
| *B32B 27/12* | (2006.01) |
| *B32B 27/32* | (2006.01) |

(52) U.S. Cl.
CPC ........ *A61F 13/15617* (2013.01); *A61F 13/15* (2013.01); *A61F 13/15593* (2013.01); *A61F 13/15699* (2013.01); *A61F 13/15739* (2013.01); *A61F 13/49* (2013.01); *A61F 13/4902* (2013.01); *A61F 13/496* (2013.01); *A61F 13/49012* (2013.01); *B29C 65/086* (2013.01); *B32B 37/04* (2013.01); *B32B 37/14* (2013.01); *A61F 2013/1591* (2013.01); *A61F 2013/15869* (2013.01); *A61F 2013/15934* (2013.01); *A61F 2013/49022* (2013.01); *B32B 5/022* (2013.01); *B32B 5/08* (2013.01); *B32B 27/08* (2013.01); *B32B 27/12* (2013.01); *B32B 27/32* (2013.01); *B32B 37/144* (2013.01); *B32B 2307/51* (2013.01); *B32B 2307/7265* (2013.01); *B32B 2555/02* (2013.01)

(58) Field of Classification Search
CPC ................ A61F 13/15617; A61F 13/15; A61F 13/15593; A61F 13/15699; A61F 13/15739; A61F 13/49; A61F 13/49012; A61F 13/4902; A61F 13/496; A61F 2013/15869; A61F 2013/1591; A61F 2013/15934; A61F 2013/49022; B29C 65/086; B32B 37/04; B32B 37/14; B32B 5/022; B32B 5/08; B32B 27/08; B32B 27/12; B32B 27/32; B32B 37/144; B32B 2307/51; B32B 2307/7265; B32B 2555/02

See application file for complete search history.

(56) References Cited

U.S. PATENT DOCUMENTS

| | | | |
|---|---|---|---|
| 2006/0057924 | A1* | 3/2006 | Cheng et al. |
| 2013/0164480 | A1 | 6/2013 | Sakurai et al. |
| 2018/0042784 | A1 | 2/2018 | Koshijima |

FOREIGN PATENT DOCUMENTS

| | | |
|---|---|---|
| JP | 2004532758 | 10/2004 |
| JP | 4508885 | 7/2010 |
| JP | 201251301 | 3/2012 |
| JP | 2012120775 | 6/2012 |
| WO | 2003000165 | 1/2003 |
| WO | 2016185999 | 11/2016 |
| WO | 2016185999 | 3/2018 |

OTHER PUBLICATIONS

International Search Report, PCT/JP2017/006999, dated May 23, 2017.

* cited by examiner

*Primary Examiner* — Alma Pipic
(74) *Attorney, Agent, or Firm* — Andrus Intellectual Property Law, LLP

(57) ABSTRACT

Ultrasonic welding is performed by passing a first sheet layer, a second sheet layer, and an elastic film interposed therebetween in a stretched state in a machine direction between an anvil roll having a large number of protrusions and an ultrasonic horn. The anvil roll includes a region having the protrusions and in the region. A site, in which welding is performed by one ultrasonic horn, has a portion in which an area rate of the protrusions changes in a roll circumferential direction and a roll length direction. A difference between a maximum value and a minimum value in a change of the area rate of the protrusions in the roll circumferential direction is 4.5% or less, and a difference between a maximum value and a minimum value in a change of the area rate of the protrusions in the roll length direction is 1.5% or less.

10 Claims, 26 Drawing Sheets

(a)

(b)

(c)

(a)

(b)

(a)

(b)

(a)

(b)

METHOD FOR FORMING ELASTIC FILM STRETCHABLE STRUCTURE, AND ABSORBENT ARTICLE

CROSS-REFERENCE TO RELATED APPLICATIONS

This application is the U.S. national stage application of International Application PCT/JP2017/006999, filed Feb. 24, 2017, which international application was published on Sep. 28, 2017, as International Publication WO 2017/163754 in the Japanese language. The International Application claims priority of Japanese Patent Application No. 2016-060316, filed Mar. 24, 2016. The international application and Japanese application are both incorporated herein by reference, in entirety.

TECHNICAL FIELD

The present invention relates to a method of forming an elastic film stretchable structure in which both front and back surface sides of an elastic film are covered with a first sheet layer and a second sheet layer, and an absorbent article having the elastic film stretchable structure.

BACKGROUND ART

In each of absorbent articles, elasticity is typically imparted to leg portions, lower torso portion, etc. to improve fitting to the surfaces of body. A typical approach to impart elasticity is attaching of elongated elastically stretchable members, such as rubber threads, in a state stretched in a longitudinal direction thereof. In order to impart elasticity in a certain range of width, rubber threads are disposed and fixed in the width direction at intervals in some embodiments. In addition, an approach to impart excellent surface fitting is attaching of elastic film in a state stretched in a direction of imparting elasticity (for example, see Patent Literature 1).

In a stretchable structure based on the elastic film (hereinafter also referred to as an elastic film stretchable structure), a stretchable region is formed by stacking an elastic film between a first sheet layer and a second sheet layer, and the first sheet layer and the second sheet layer are bonded via through-holes formed in the elastic film at a large number of dot-like sheet bonded portions arranged at intervals in a stretchable direction and a direction orthogonal thereto respectively while the elastic film is stretched in the stretchable direction along the surfaces thereof. In such an elastic film stretchable structure, in a natural length state, as the elastic film contracts between the sheet bonded portions, intervals between two adjacent sheet bonded portions are decreased, and contraction wrinkles extending in the direction orthogonal to the stretchable direction are formed between the sheet bonded portions in the first sheet layer and the second sheet layer. On the contrary, in a stretched state, as the elastic film is stretched between the sheet bonded portions, the intervals between the sheet bonded portions are increased and the contraction wrinkles in the first sheet layer and the second sheet layer are extended, and elastic stretching is allowed so that the first sheet layer and the second sheet layer can be completely spread. This elastic film stretchable structure has advantages as follows: surface fitting is excellent; the first sheet layer and the second sheet layer are not bonded to the elastic film and bonded each other but at an extremely low level, thus the elastic film stretchable structure has a satisfactory flexibility; and the through-holes of the elastic film contribute to improvement in air permeability.

In this elastic film stretchable structure, it is found that stretching stress or elongation at an elastic limit changes depending on the area rate of the sheet bonded portions. Further, it is found that the stretching stress or elongation at the elastic limit depending on the sites is obtained using this phenomenon by providing the elastic film stretchable structure throughout extensive sites of an article and providing a plurality of regions having different area rates of the sheet bonded portions therein.

Meanwhile, the elastic film stretchable structure described above may be manufactured by forming the sheet bonded portions by bonding the first sheet layer and the second sheet layer at a large number of positions arranged at intervals in a state in which the elastic film is interposed between the first sheet layer and the second sheet layer while being stretched in the stretchable direction. In this instance, the elastic film stretchable structure having stretching stresses or elongations at the elastic limit depending on the sites is obtained by arranging the sheet bonded portions in a pattern including a plurality of regions having different area rates. Heat sealing or a hot-melt adhesive can be used as a bonding scheme of the first sheet layer and the second sheet layer. However, it is desirable to adopt ultrasonic welding, because bonding may be performed in a fine pattern, and decrease in flexibility is small in the ultrasonic welding.

FIG. 20 illustrates an example of an ultrasonic sealing apparatus. In the ultrasonic sealing apparatus, to form sheet bonded portions 40, a first sheet layer 20A, an elastic film 30, and a second sheet layer 20B are fed between an ultrasonic horn 61 and an anvil roll 60 having protrusions 60a formed in a pattern of the sheet bonded portions 40 on an external surface. In this instance, for example, when a feed speed of conveyance of the elastic film 30 at an upstream side by a feed drive roll 63 and a nip roll 62 is controlled to be lower than a feed speed of conveyance after the anvil roll 60 and the ultrasonic horn 61, the elastic film 30 is stretched to a predetermined stretch rate in an MD (machine direction, flow direction) on a path from a nip position by the feed drive roll 63 and the nip roll 62 to a sealing position by the anvil roll 60 and the ultrasonic horn 61. Reference symbol 62 denotes the nip roll. The first sheet layer 20A, the elastic film 30, and the second sheet layer 20B fed between the anvil roll 60 and the ultrasonic horn 61 are, in a stacked state in this order, heated by ultrasonic vibration energy of the ultrasonic horn 61 while being pressed between the protrusions 60a and the ultrasonic horn 61. Further, the through-holes 31 are formed in the elastic film 30 by melting only the elastic film 30 or melting the elastic film 30 and at least one of the first sheet layer 20A and the second sheet layer 20B. At the same time, the first sheet layer 20A and the second sheet layer 20B are bonded via the through-holes 31. Therefore, the area rate of the sheet bonded portions 40 may be changed in at least one of the MD and a CD (cross direction) by providing regions of a plurality of patterns having different sizes, shapes, and arrangements (intervals between adjacent sheet bonded portions in a roll length direction and those in a roll circumferential direction) of the protrusions 60a such that the area rate of the protrusions 60a of the anvil roll 60 changes in at least one of the roll circumferential direction and the roll length direction.

However, the following problem has been found. When a change in area rate of the protrusions 60a of the anvil roll 60 in at least one of a roll circumferential direction RD and a roll length direction QD is great as illustrated in FIGS. 22(a) and 22(c), thermal expansion of the anvil roll 60 or the ultrasonic horn 61 becomes larger in a high-area-rate-region 60H in which the area rate of the protrusions 60a is high than in a low-area-rate-region 60L in which the area rate of the protrusions 60a is low during a long time operation. Accordingly, contact between the elastic film and the ultrasonic horn 61 is weakened in the low-area-rate-region 60L in which the area rate is low, and a welding defect (insufficient welding or non-welding) is caused.

For example, as illustrated in a development figure of a peripheral surface of the anvil roll 60 of FIG. 22(a), in a mode in which the area is changed from the low-area-rate-region 60L having the low area rate of the protrusions 60a to the high-area-rate-region 60H having the high area rate of the protrusions 60a in the roll circumferential direction RD and then, the area rate is changed from the high-area-rate-region 60H to the low-area-rate-region 60L, if a difference in area rate therebetween is large, for example, about 8%, the high-area-rate-region 60H of the protrusions 60a in the anvil roll 60 will thermally expand to a higher degree as illustrated in FIG. 22(b) during the longtime operation. Even though the ultrasonic horn 61 thermally expands, there is no problem when expansion is uniform in the CD, and thus illustration is omitted in the figure. Therefore, during a longtime operation, immediately after a clearance of the ultrasonic horn 61 becomes large due to the region in which the thermal expansion is large (the high-area-rate-region 60H), welding is performed for the region in which the thermal expansion is small (the low-area-rate-region 60L). Thus, due to lack of time to control the clearance of the ultrasonic horn 61, welding defects are likely to occur.

In addition, as illustrated in a development figure of the peripheral surface of the anvil roll 60 of FIG. 22(c), in a mode in which the area rate of the protrusions 60a changes in the roll length direction QD such as a mode of having the low-area-rate-region 60L in which the area rate of the protrusions 60a is low on one side in the roll length direction QD and having the high-area-rate-region 60H in which the area rate of the protrusions 60a is high on the other side in the roll length direction QD, if a difference in area rate therebetween is large, for example, about 4%, the high-area-rate-region 60H of the protrusions 60a in the anvil roll 60 will thermally expand to a higher degree as illustrated in FIG. 22(d) during a long time operation. In addition, a portion of the ultrasonic horn 61 facing the high-area-rate-region 60H of the protrusions 60a of the anvil roll 60 in the CD will thermally expand to a higher degree. Therefore, during a long time operation, the clearance of the ultrasonic horn 61 is controlled in accordance with the region in which the thermal expansion is large in the CD. In such a case, welding should be performed in a state in which the clearance is excessively large at all times even in the region in which the thermal expansion is small in the CD. Thus, a welding defect is likely to occur in the region in which thermal expansion is small.

CITATION LIST

Patent Literature

Patent Literature 1: JP 2004-532758 A

SUMMARY OF INVENTION

Technical Problem

In this regard, a main object of the invention is to prevent a welding defect in a method of forming an elastic film stretchable structure by ultrasonic welding.

Solution to Problem

Representative aspects of the invention solving the above-mentioned problem are as follows.

<First Aspect>

A method of forming an elastic film stretchable structure comprising:

a supply step of interposing an elastic film between a first sheet layer and a second sheet layer in a stretched state in a machine direction (MD); and a bonding step of passing the first sheet layer, the second sheet layer, and the elastic film interposed therebetween in the stretched state, between an anvil roll having a plurality of protrusions arranged at intervals in a predetermined pattern on an outer peripheral surface, and at least one ultrasonic horn facing the outer peripheral surface of the anvil roll, and forming sheet bonded portions by welding the first sheet layer and the second sheet layer only at portions interposed between the plurality of protrusions and the ultrasonic horn, wherein the anvil roll includes a region having the protrusions, the region includes a site in which welding is performed by at least one ultrasonic horn, the site has a portion in which an area rate of the protrusions changes in a roll circumferential direction, and a difference between a maximum value and a minimum value in a change of the area rate of the protrusions in the roll circumferential direction is 4.5% or less.

(Operational Advantage)

The difference between the maximum value and the minimum value in a change of the area rate of the protrusions in the roll circumferential direction of the anvil roll is set to 4.5% or less in this way, which makes a difference in thermal expansion in the roll circumferential direction small during a long time operation. Thus, the lack of time to control the clearance of the ultrasonic horn rarely occurs, and a welding defect is hardly caused. A method of obtaining the difference between the maximum value and the minimum value in the change of the area rate of the protrusions (equivalent to the sheet bonded portions) will be described below.

<Second Aspect>

A method of forming an elastic film stretchable structure comprising:

a supply step of interposing an elastic film between a first sheet layer and a second sheet layer in a stretched state in an MD; and a bonding step of passing the first sheet layer, the second sheet layer, and the elastic film interposed therebetween in the stretched state, between an anvil roll having a plurality of protrusions arranged at intervals in a predetermined pattern on an outer peripheral surface, and at least one ultrasonic horn facing the outer peripheral surface of the anvil roll, and forming sheet bonded portions by welding the first sheet layer and the second sheet layer only at portions interposed between the plurality of protrusions and the ultrasonic horn, wherein the anvil roll includes a region having the protrusions, the region includes a site in which welding is performed by at least one ultrasonic horn, the site has a portion in which an area rate of the protrusions changes in a roll length direction, and a difference between a maximum value and a minimum value in a change of the area rate of the protrusions in the roll length direction is 1.5% or less.

(Operational Advantage)

The difference between the maximum value and the minimum value in the change of the area rate of the protrusions in the roll length direction of the anvil roll is set to 1.5% or less in this way, which makes a difference in thermal expansion in the roll length direction small during a long time operation. Thus, a clearance between the ultrasonic horn and the anvil roll rarely becomes excessively large in a region in which thermal expansion is small in the CD, and a welding defect hardly occurs. A method of obtaining the difference between the maximum value and the minimum value in the change of the area rate of the protrusions (equivalent to the sheet bonded portions) will be described below.

<Third Aspect>

A method of forming an elastic film stretchable structure comprising:

a supply step of interposing an elastic film between a first sheet layer and a second sheet layer in a stretched state in an MD; and a bonding step of passing the first sheet layer, the second sheet layer, and the elastic film interposed therebetween in the stretched state, between an anvil roll having a plurality of protrusions arranged at intervals in a predetermined pattern on an outer peripheral surface, and at least one ultrasonic horn facing the outer peripheral surface of the anvil roll, and forming sheet bonded portions by welding the first sheet layer and the second sheet layer only at portions interposed between the plurality of protrusions and the ultrasonic horn, wherein the anvil roll includes a region having the protrusions, the region includes a site in which welding is performed by at least one ultrasonic horn, the site has a portion in which an area rate of the protrusions changes in a roll circumferential direction and a roll length direction, a difference between a maximum value and a minimum value in a change of the area rate of the protrusions in the roll circumferential direction is 4.5% or less, and a difference between a maximum value and a minimum value in a change of the area rate of the protrusions in the roll length direction is 1.5% or less.

(Operational Advantage)

Operational advantages of both the first aspect and the second aspect are achieved.

<Fourth Aspect>

The method of forming an elastic film stretchable structure according to any one of the first to third aspects, wherein in the bonding step, for the single anvil roll, a plurality of ultrasonic horns is arranged in a cross direction (CD) to face a range in a roll length direction having the protrusions of the single anvil roll, and the welding is performed between the single anvil roll and the respective plurality of ultrasonic horns, and the region having the plurality of protrusions of the single anvil roll has a difference of 1.5% or less between a maximum value and a minimum value in a change of the area rate of the protrusions in the roll length direction for each site in which welding is performed by each ultrasonic horn.

(Operational Advantage)

In ultrasonic welding, when a width of the ultrasonic horn increases, a welding defect in the roll length direction described above is likely to occur. Thus, in a case in which ultrasonic welding is performed for a certain length or for longer than the certain length in the CD, it is desirable to perform a process by arranging a plurality of ultrasonic horns for one anvil roll. Further, in this case, even though the difference between the maximum value and the minimum value in the change of the area rate of the protrusions may be set with respect to all protrusions of one anvil roll, it is desirable that the difference between the maximum value and the minimum value in the change of the area rate of the protrusions in the roll length direction is set to 1.5% or less for each site in which welding is performed by each ultrasonic horn as in this fourth aspect.

<Fifth Aspect>

The method of forming an elastic film stretchable structure according to any one of the first to fourth aspects, wherein a melting point of the first sheet layer and the second sheet layer is 85 to 190° C., a melting point of the elastic film is 80 to 145° C., and a difference between the melting point of the first sheet layer and the second sheet layer and the melting point of the elastic film is 60 to 80° C.

(Operational Advantage)

The above specified differences between the maximum values and the minimum values in the change of the area rates of the protrusions in the first to fourth aspects are particularly effective under the conditions of the fifth aspect.

<Sixth Aspect>

An absorbent article comprising an absorber that absorbs excrement, wherein the absorbent article has an elastic film stretchable structure in which an elastic film is stacked between a first sheet layer and a second sheet layer and the first sheet layer and the second sheet layer are bonded via through-holes penetrating the elastic film at a plurality of sheet bonded portions arranged at intervals, a region having the elastic film stretchable structure has a plurality of bonded regions in which area rates of the sheet bonded portions are different from each other, the region having the elastic film stretchable structure includes a site totally in a stretchable direction and at least partly in a direction orthogonal to the stretchable direction, the site has a portion in which an area rate of the sheet bonded portions changes in the stretchable direction, and a difference between a maximum value and a minimum value in a change of the area rate of the sheet bonded portions in the stretchable direction is 4.5% or less.

(Operational Advantage)

Such an elastic film stretchable structure is excellent in structural homogeneity in the stretchable direction in the region having the elastic film stretchable structure, and thus has more uniform texture, flexibility, elasticity, etc. In addition, such an elastic film stretchable structure may be formed by the first aspect. In this case, the sheet bonded portions are formed to have substantially the same size and arrangement of those of the protrusions of the anvil roll, and thus the same operational advantage as that in the first aspect is achieved.

<Seventh Aspect>

An absorbent article comprising an absorber that absorbs excrement, wherein the absorbent article has an elastic film stretchable structure in which an elastic film is stacked between a first sheet layer and a second sheet layer and the first sheet layer and the second sheet layer are bonded via through-holes penetrating the elastic film at a plurality of sheet bonded portions arranged at intervals, a region having the elastic film stretchable structure has a plurality of bonded regions in which area rates of the sheet bonded portions are different from each other, the region having the elastic film stretchable structure includes a site totally in a stretchable direction and at least partly in a direction orthogonal to the stretchable direction, the site has a portion in which an area rate of the sheet bonded portions changes in the direction orthogonal to the stretchable direction, and a difference between a maximum value and a minimum value in a change of the area rate of the sheet bonded portions in the direction orthogonal to the stretchable direction is 1.5% or less.

(Operational Advantage)

Such an elastic film stretchable structure is excellent in structural homogeneity in the direction orthogonal to the stretchable direction in the region having the elastic film stretchable structure, and thus has more uniform texture, flexibility, elasticity, etc. In addition, such an elastic film stretchable structure may be formed by the second aspect. In this case, the sheet bonded portions are formed to have substantially the same size and arrangement of those of the protrusions of the anvil roll, and thus the same operational advantage as that in the second aspect is achieved.

<Eighth Aspect>

An absorbent article comprising an absorber that absorbs excrement, wherein the absorbent article has an elastic film stretchable structure in which an elastic film is stacked between a first sheet layer and a second sheet layer and the first sheet layer and the second sheet layer are bonded via through-holes penetrating the elastic film at a plurality of sheet bonded portions arranged at intervals, a region having the elastic film stretchable structure has a plurality of bonded regions in which area rates of the sheet bonded portions are different from each other, the region having the elastic film stretchable structure includes a site totally in a stretchable direction and at least partly in a direction orthogonal to the stretchable direction, and the site has a portion in which an area rate of the sheet bonded portions changes in the stretchable direction and the direction orthogonal to the stretchable direction, a difference between a maximum value and a minimum value in a change of the area rate of the sheet bonded portions in the stretchable direction is 4.5% or less, and a difference between a maximum value and a minimum value in a change of the area rate of the sheet bonded portions in the direction orthogonal to the stretchable direction is 1.5% or less.

(Operational Advantage)

Such an elastic film stretchable structure is excellent in structural homogeneity in the stretchable direction and the direction orthogonal to the stretchable direction in the region having the elastic film stretchable structure, and thus has more uniform texture, flexibility, elasticity, etc. In addition, such an elastic film stretchable structure may be formed by the third aspect. In this case, the sheet bonded portions are formed to have substantially the same size and arrangement of those of the protrusions of the anvil roll, and thus the same operational advantage as that in the third aspect is achieved.

<Ninth Aspect>

The absorbent article according to any one of the sixth to eighth aspects, wherein the region having the elastic film stretchable structure includes a non-stretchable region, and either one of or both of a stretchable region adjacent to at least one side of the non-stretchable region in the stretchable direction and a stretchable region adjacent to at least one side of the non-stretchable region in the direction orthogonal to the stretchable direction, and an area rate of the sheet bonded portions is higher in the non-stretchable region than in the stretchable region.

(Operational Advantage)

In the elastic film stretchable structure of the invention, elasticity may be substantially canceled by increasing the area rate of the sheet bonded portions. However, in this case, a change in the area rate of the sheet bonded portions tends to be large. Therefore, features of the sixth to eighth aspects described above have technical significance in the case of the ninth aspect.

<Tenth Aspect>

The absorbent article according to any one of the sixth to ninth aspects, wherein the absorbent article is an underpants-type disposable diaper including an outer member disposed in a front body and a back body provided individually or as one unit, and an inner member including the absorber and attached to the outer member, both side portions of the outer member in the front body and both side portions of the outer member in the back body being bonded, respectively, and having a waist opening and a pair of left and right leg openings, and the outer member in at least one of the front body and the back body has the elastic film stretchable structure throughout a range including a whole of the width direction thereof such that a stretchable direction thereof is the width direction.

(Operational Advantage)

The underpants-type disposable diaper particularly attaches importance to surface fitting among absorbent articles, and requires a wide stretchable region. Therefore, the fifth to ninth aspects are suitable for the stretchable region of such an underpants-type disposable diaper. For the same reason, the first to fifth aspects are suitable for manufacturing the outer member of the underpants-type disposable diaper.

Advantageous Effects of Invention

According to the invention, there is an advantage that a welding defect may be prevented in a method of forming an elastic film stretchable structure by ultrasonic welding, etc.

DESCRIPTION OF EMBODIMENTS

Figure 1:
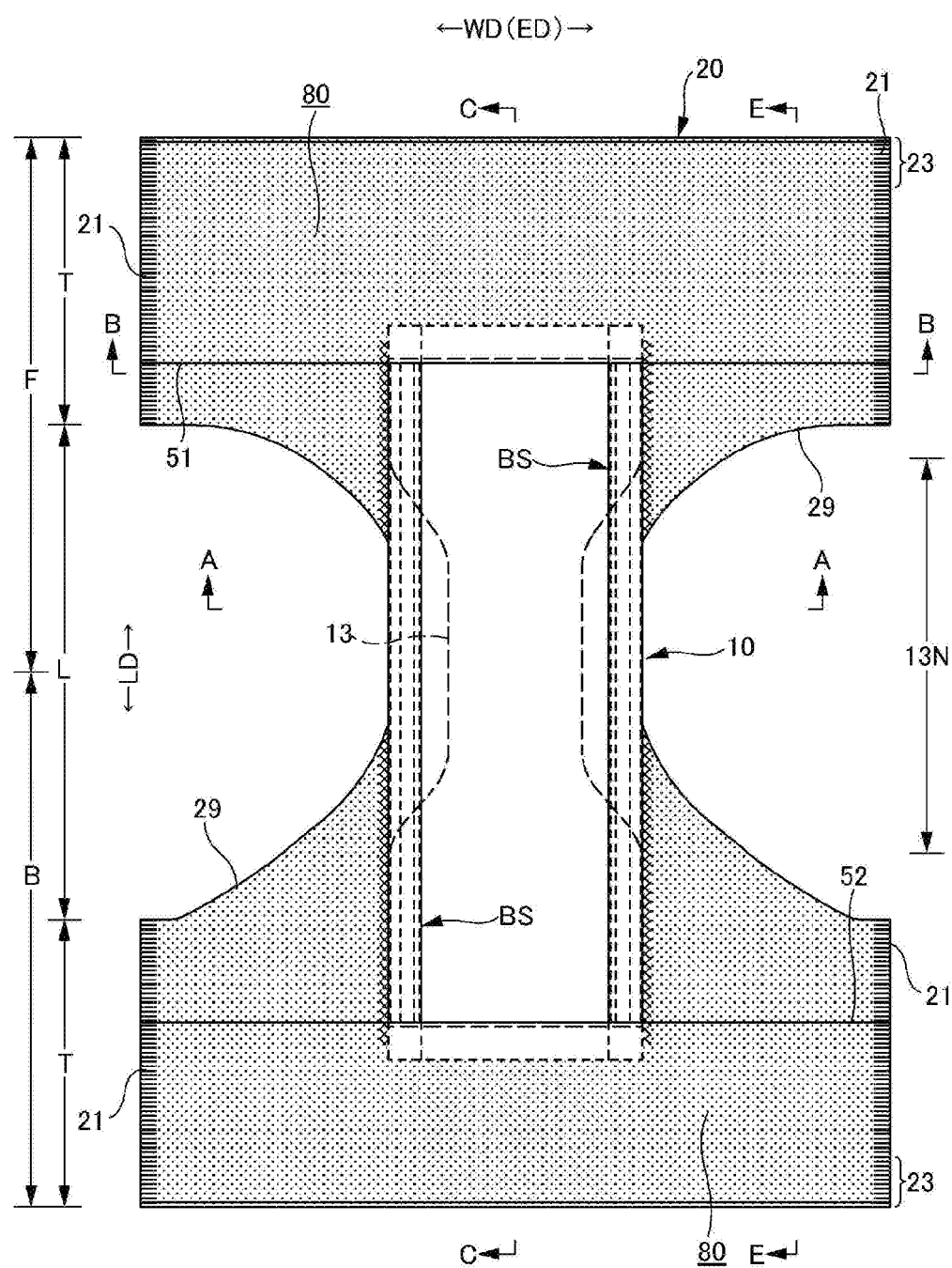
FIG. 1 is a plan view (internal surface side) of an underpants-type disposable diaper in a spread state.

Hereinafter, an embodiment of the invention will be described with reference to accompanying drawings. A dotted portion in a cross-sectional view indicates bonding means such as a hot-melt adhesive.

FIG. 1 to FIG. 6 illustrate an underpants-type disposable diaper. This underpants-type disposable diaper (hereinafter also simply referred to as a diaper) has an outer member 20 disposed in a front body F and a back body B and an inner member 10 attached to the outer member 20 as one unit. Further, in the inner member 10, is formed by interposing an absorber 13 between a liquid pervious top sheet 11 and a liquid impervious sheet 12. In manufacturing, after a back surface of the inner member 10 is bonded to the internal surface (upper surface) of the outer member 20 using bonding means such as a hot-melt adhesive, the inner member 10 and the outer member 20 are folded at a center in a front-back direction LD (vertical direction) corresponding to a boundary between the front body F and the back body B, both side portions thereof are bonded to each other by heat sealing, a hot-melt adhesive, etc. to form side seal portions 21, and a waist opening and a pair of right and left leg openings are formed.

(Exemplary Structure of Inner Member)

Figure 4:
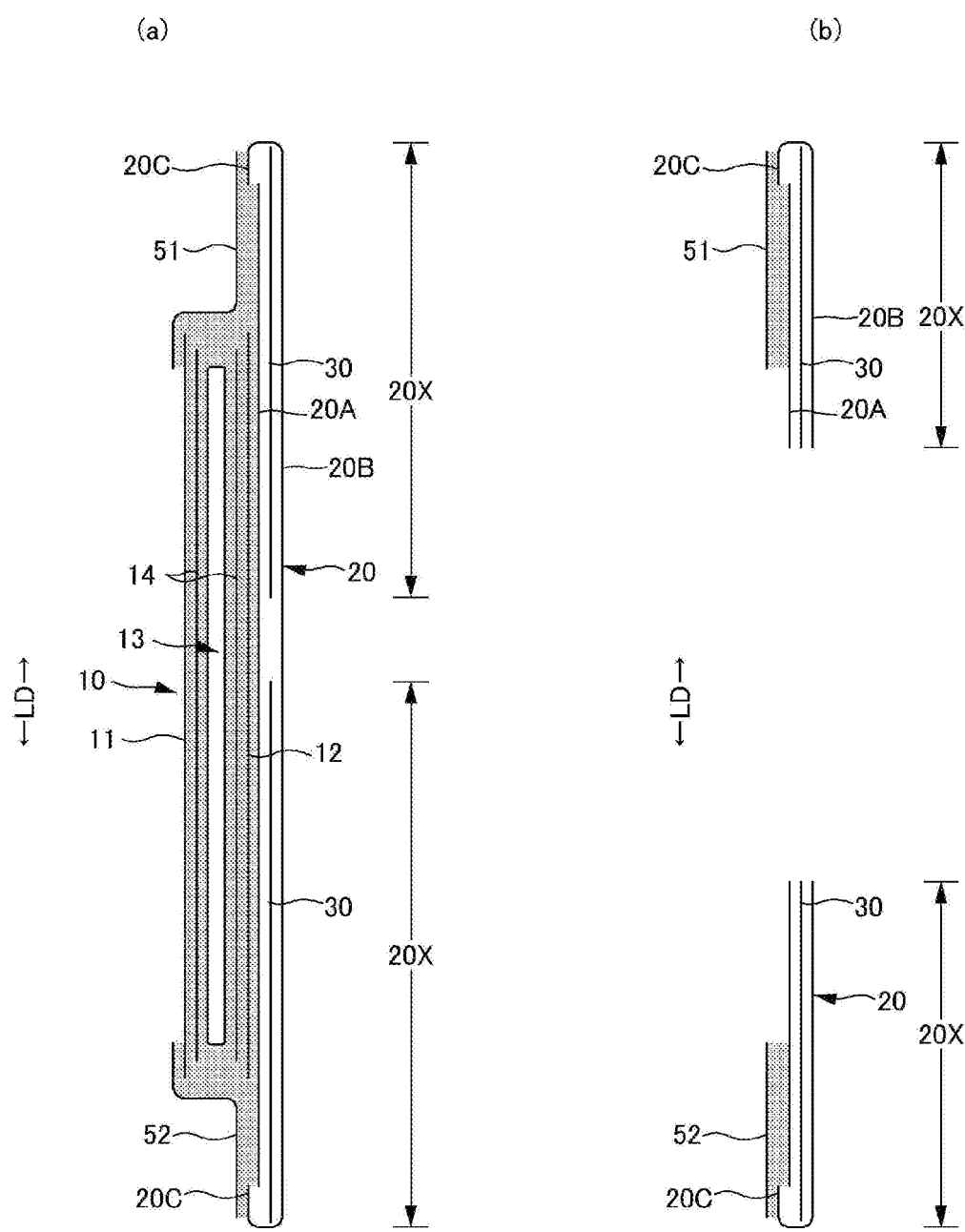
FIG. 4(a) is a C-C cross-sectional view of FIG. 1.
FIG. 4(b) is an E-E cross-sectional view of FIG. 1.
Figure 5:
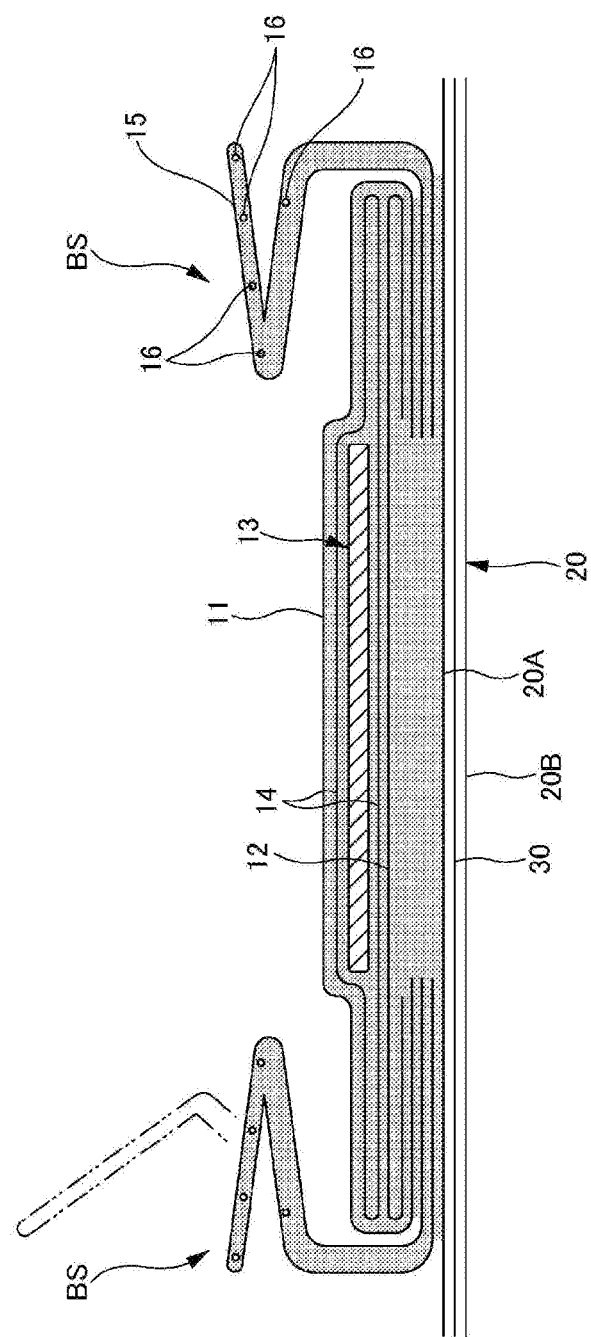
FIG. 5 is an A-A cross-sectional view of FIG. 1.
Figure 6:
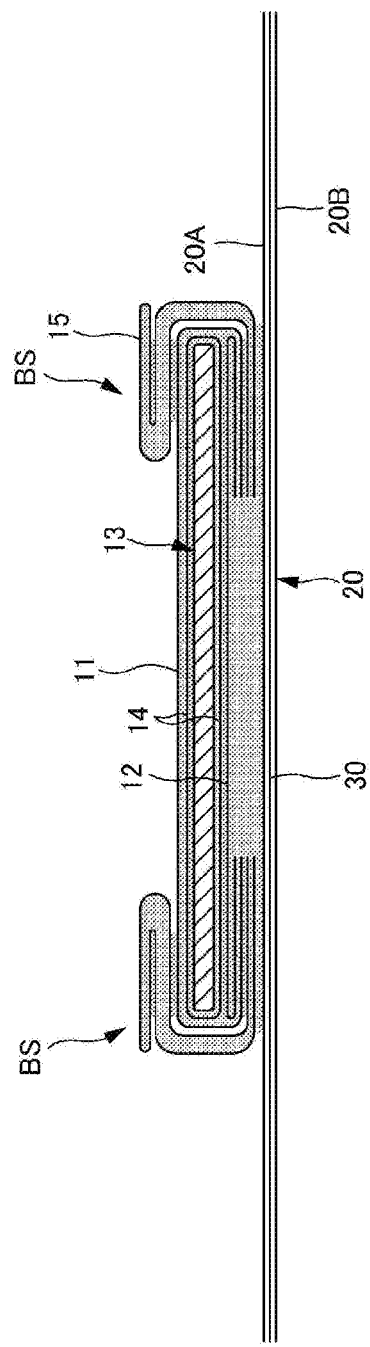
FIG. 6 is a B-B cross-sectional view of FIG. 1.

As illustrated in FIGS. 4 to 6, the inner member 10 has a structure in which the absorber 13 is interposed between the liquid pervious top sheet 11 and the liquid impervious sheet 12 made of polyethylene, etc., and absorbs and retains excretory fluid passing through the top sheet 11. The inner member 10 may have any planar shape and typically has a substantially rectangular shape as shown in FIG. 1.

The liquid pervious top sheet 11 that covers a front surface side (skin side) of the absorber 13 is preferably composed of perforated or imperforate nonwoven fabric or a porous plastic sheet. Examples of the raw fibers of the nonwoven fabric include synthetic fibers, such as olefin fibers, e.g., polyethylene and polypropylene, polyester fibers, and polyamide fibers; recycled fibers, such as rayon and cupra; and natural fibers, such as cotton. The nonwoven fabric can be produced by any process, for example, spun lacing, spun bonding, thermal bonding, melt blowing, or needle punching. Among these processes, preferred are spun lacing in view of flexibility and drape characteristics and thermal bonding in view of bulky soft products. A large number of through-holes formed in the liquid pervious top sheet 11 facilitate absorption of urine and achieve dry touch characteristics. The liquid pervious top sheet 11 extends around side edge portions of the absorber 13 and extends to the back surface side of the absorber 13.

For example, a liquid impervious plastic sheet such as polyethylene sheet or polypropylene sheet is used as the liquid impervious sheet 12 that covers the back surface side (non-skin contact side) of the absorber 13. Recently, permeable sheets have been preferably used in view of preventing stuffiness. This water-block permeable sheet is a micro-porous sheet prepared through melt-kneading an olefin resin, for example, polyethylene resin or polypropylene resin, and inorganic filler, forming a sheet with the kneaded materials, and then uniaxially or biaxially stretching the sheet.

The absorber 13 may be composed of a well-known basic component, such as an accumulated body of pulp fibers, an assembly of filaments, composed of, for example, cellulose acetate, or nonwoven fabric, and the absorber 13 may include as necessary high-absorbent polymer mixed or fixed to the basic component. The absorber 13 may be wrapped with a liquid-permeable and liquid-retainable wrapping sheet 14, such as a crepe sheet, to retain the shape and polymers, as required.

The absorber 13 has a substantially hourglass shape having at a crotch portion, a narrowing part 13N with a width being narrower than those of the both front and back sides. However, it is possible to adopt an appropriate shape such as a rectangular shape. The size of the narrowing part 13N may be appropriately determined. The length of the narrowing part 13N in the front-back direction LD may be set to about 20 to 50% of the entire length of the diaper, and the width of a narrowest part thereof may be set to about 40 to 60% of the entire width of the absorber 13. When the inner body 10 has a substantially rectangular planar shape in the case of the absorber with such a narrowing part 13N, the inner member 10 has non-absorber side portions free of the absorber 13 according to the narrowing part 13N of the absorber 13.

Three-dimensional gathers BS, which are configured to fit around the legs, are formed on the both side portions of the inner member 10. As illustrated in FIG. 5 and FIG. 6, each of the three-dimensional gathers BS is formed by folding a gather nonwoven fabric 15 into a duplicate sheet, including a fixed portion fixed to a side portion of the back surface of the inner member; a main body portion extending from the fixed portion around the side of the inner member to the side portion of the front surface of the inner member; fallen portions formed by fixing the front end portion and back end portion of the main body portion to the side portion of the front surface of the inner member in a fallen state; and a free part formed in an un-fixed state between the fallen portions.

In addition, elongated gather elastic members 16 are disposed, for example, at a tip portion of the free part, between double sheets. As indicated by a two-dot chain line in FIG. 5, the free part is erected by elastic stretching force of the gather elastic members 16 to form the three-dimensional gather BS in a product state.

The liquid impervious sheet 12 is folded back to the back surface side together with the liquid pervious top sheet 11 at both sides of the absorber 13 in the width direction WD. It is desirable that the liquid impervious sheet 12 is opaque to block transmission of brown color of stool and urine. Preferred examples of the opacifying agent compounded in the plastic film include colorant or filler, such as calcium carbonate, titanium oxide, zinc oxide, white carbon, clay, talc, and barium sulfate.

The gather elastic member 16 may be composed of commodity materials, for example, styrene rubber, olefin rubber, urethane rubber, ester rubber, polyurethanes, polyethylene, polystyrene, styrene-butadiene, silicones, and polyester. The gather elastic members 16 preferably have a fineness of 925 dtex or less and are disposed under a tension of 150% to 350% at an interval of 7.0 mm or less to be hidden from outside view. The gather elastic member 16 may have a string shape shown in the drawing or a tape shape with an appropriate width.

Like the liquid pervious top sheet 11, the gather nonwoven fabric 15 may be composed of raw fibers including synthetic fibers, such as olefin fibers of, for example, polyethylene fibers or polypropylene fibers; polyester fibers and amide fibers; recycled fibers of, for example, rayon and cupra; and natural fibers such as cotton. The gather nonwoven fabric may be prepared by any appropriate process, for example, spun bonding, thermal bonding, melt blowing, or needle punching. In particular, the basis weight should be reduced for production of a nonwoven fabric that can prevent stuffiness and has high air permeability. It is desirable that the gather nonwoven fabric 15 is a water-repellent nonwoven fabric coated with a water repellent agent, for example, a silicone-based agent, a paraffin-metallic agent, or an alkyl chromic chloride agent to prevent permeability of urine, etc., to prevent diaper rash, and to enhance feeling to skin (dryness).

Figure 3:
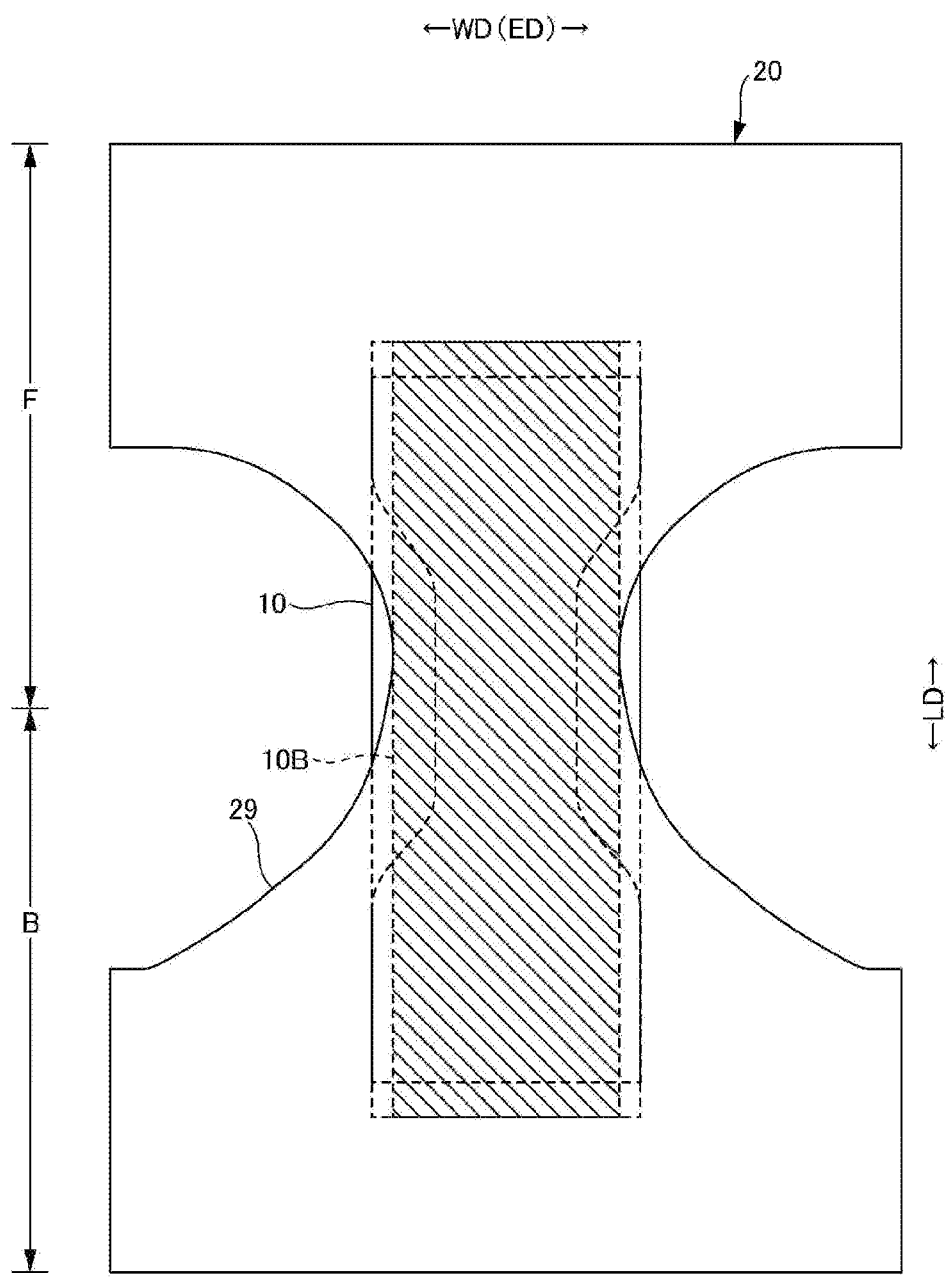
FIG. 3 is a plan view illustrating only a main part of the underpants-type disposable diaper in the spread state.

As illustrated in FIG. 3, the back surface of the inner member 10 is fixed to the internal surface of the outer member 20 by a hot-melt adhesive, etc. in an internal and external fixed region 10B (shaded area). The internal and external fixed region 10B extends from a front side to a back side of a range having the narrowing part 13N of the absorber 13 in the front-back direction LD. Side edges of the internal and external fixed region 10B are preferably positioned at lateral sides of a middle of a range overlapping the narrowing part 13N of the absorber 13 in the width direction WD. In particular, it is preferable that the internal and external fixed region 10B is fixed to the outer member 20 throughout substantially the entire part in the width direction WD and the substantially the entire part in the front-back direction LD in the inner member 10.

(Front and Back Cover Sheets)

As illustrated in FIG. 1 and FIG. 4, front and back cover sheets 51 and 52 may be provided to cover the front and back end portions of the inner member 10 attached to the internal surface of the outer member 20 and to prevent leakage from the front and back edges of the inner member 10. The illustrated mode will be described in more detail. The front cover sheet 51 extends along a whole part in the width direction WD of the front body F on the internal surface of the outer member 20 from an internal surface of the folded part 20C in a waist region 23 to a position overlapping with a front end portion of the inner member 10. The back cover sheet 52 extends along a whole part in the width direction WD of the back body B on the internal surface of the outer member 20 from the internal surface of the folded part 20C in the waist region 23 to a position overlapping with the back end portion of the inner member 10. Minor non-bonded regions may be provided along a whole part in the width direction WD (or only at a central portion) at edge portions of the front and back cover sheets 51 and 52 on the crotch side. The front and back cover sheets 51 and 52 having such non-bonded regions can prevent leakage of the adhesive and function as barriers against leakage when slightly suspended from the top sheet.

As in the illustrated mode, when the front and back cover sheets 51 and 52 are attached as separate components, there is an advantage that a range of choice of material is enlarged. However, there is a disadvantage that materials and manufacturing processes increase. Thus, the folded part 20C formed by folding back the outer member 20 toward the inner surface side of the diaper are respectively extended to portions overlapping with the inner member 10 to have the same function as that of the cover sheets 51 and 52.

(Structure Example of Outer Member)

Figure 7:
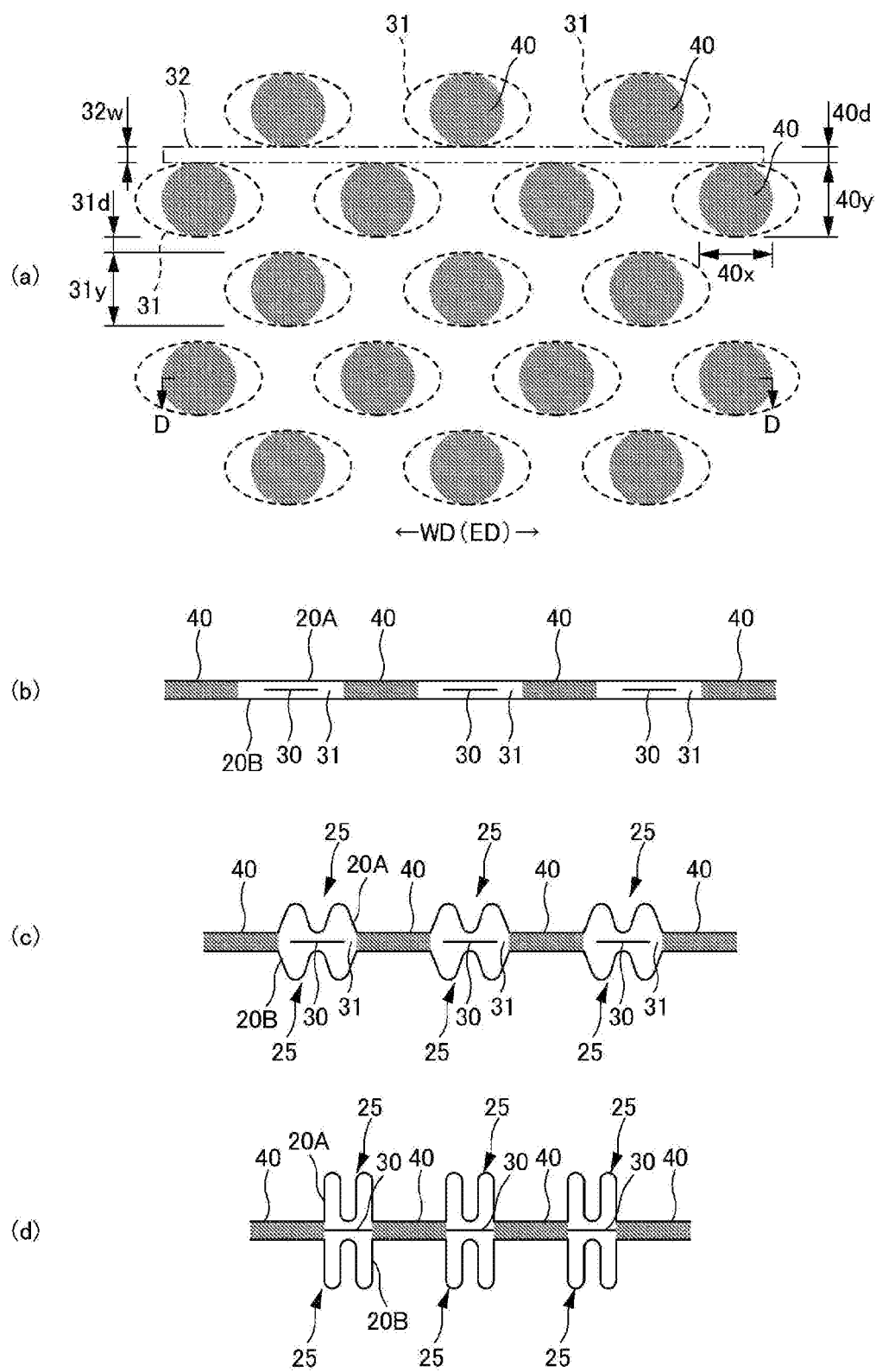
FIG. 7(a) is a plan view of a main part of a stretchable region.
FIG. 7(b) is a D-D cross-sectional view of FIG. 7(a)
FIG. 7(c) is a cross-sectional view in a worn state.
FIG. 7(d) is a cross-sectional view in a natural length state.

As long as the outer member 20 is extended from the side edge of the absorber 13 to a lateral side thereof, referring to the outer member 20, in the crotch portion, a side edge of the outer member 20 may be positioned closer to a central side than a side edge of the inner member 10 in the width direction WD as in the illustrated mode, or may be positioned closer to an outer side than the side edge of the inner member 10 in the width direction WD. In addition, the outer member 20 has a lower torso portion T corresponding to a range in the front-back direction LD of each side seal portion 21, and an intermediate portion L corresponding to a range in the front-back direction LD between the lower torso portion T of the front body F and the lower torso portion T of the back body B. Further, in the outer member 20 of the illustrated mode, except for the middle of the intermediate region L in the front-back direction LD, an elastic film 30 is stacked between a first sheet layer 20A and a second sheet layer 20B as illustrated in FIG. 2 and FIG. 4 to FIG. 6, and the first sheet layer 20A and the second sheet layer 20B have an elastic film stretchable structure 20X, a stretchable direction ED of which is corresponding to the width direction WD, are bonded via through-holes 31 penetrating the elastic film 30 at a large number of sheet bonded portions 40 arranged at intervals as illustrated in FIG. 7. A planar shape of the outer member 20 is formed including concave-shaped leg lines 29 such that both side edges of the intermediate portion L in the width direction WD form the leg openings, and corresponds to a shape similar to an hourglass as a whole. The outer member 20 may be divided into the front body F and the back body B and disposed such that the front body F and the back body B are spaced apart from each other in the front-back direction LD in the crotch portion.

Figure 2:
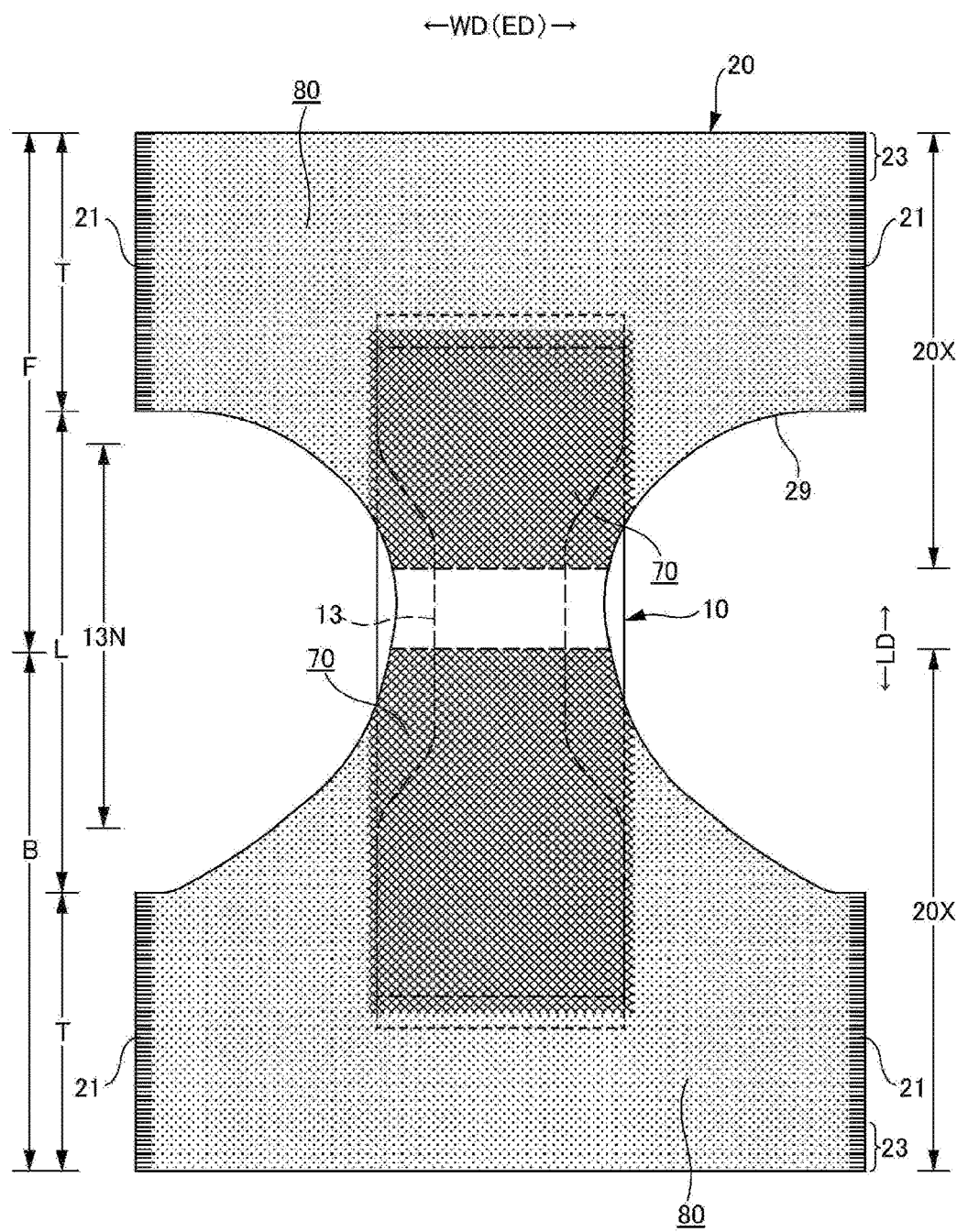
FIG. 2 is a plan view (external surface side) of the underpants-type disposable diaper in the spread state.
Figure 15:
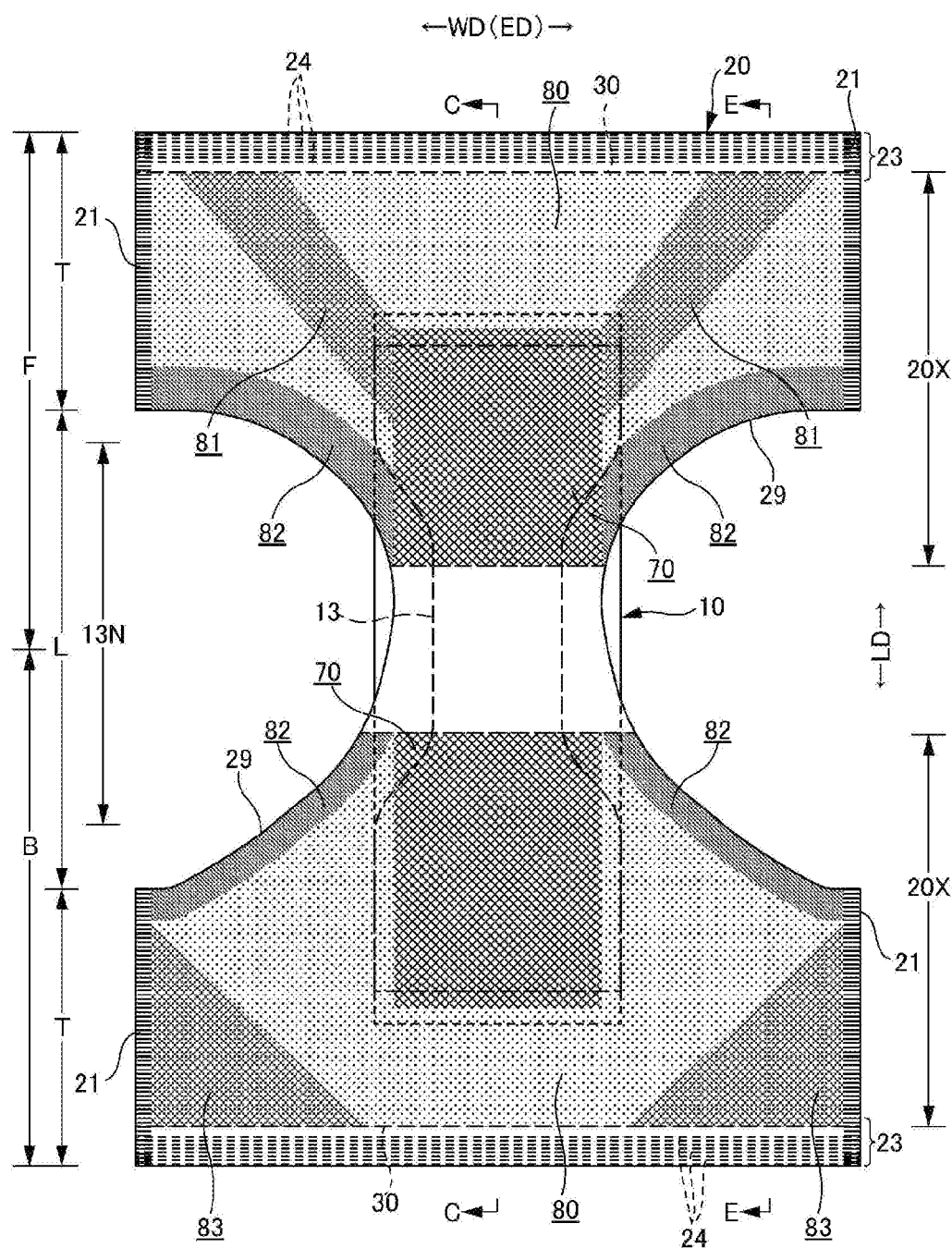
FIG. 15 is a plan view (external surface side) of the underpants-type disposable diaper in the spread state.
Figure 16:
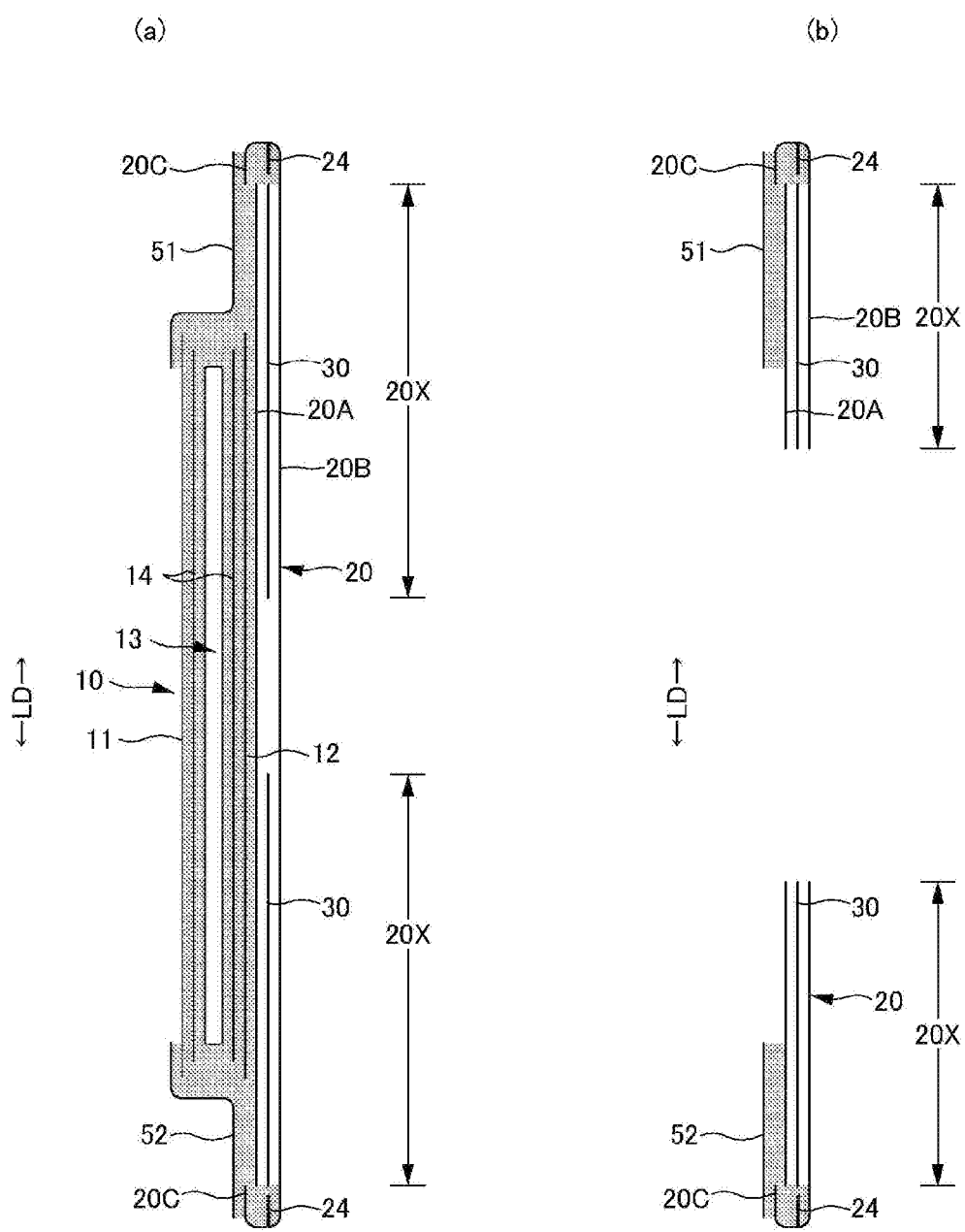
FIG. 16(a) is a C-C cross-sectional view of FIG. 15.
FIG. 16(b) is an E-E cross-sectional view of FIG. 15.

The modes illustrated in FIG. 1 and FIG. 2 correspond to a mode in which the elastic film stretchable structure 20X extends to the waist region 23. However, when the elastic film stretchable structure 20X is used in the waist region 23, tightening of the waist region 23 is insufficient. It is possible to provide a stretchable structure 20X according to conventional elongated waist portion elastic members 24 as necessary without providing the elastic film stretchable structure 20X in the waist region 23 as illustrated in FIG. 15 and FIG. 16. The waist portion elastic members 24 correspond to elongated elastic members such as a plurality of rubber threads disposed at intervals in the front-back direction LD, and apply a stretching force to tighten around the waist of the body. The waist portion elastic members 24 are not disposed substantially in a bundle with a close spacing, and three or more, preferably five or more members are disposed at intervals of about 3 to 8 mm to form a predetermined stretchable zone. A stretch rate of the waist portion elastic members 24 in fixing may be appropriately determined. However, the stretch rate may be set to about 230 to 320% in the case of normal adult use. Rubber threads are used as the waist portion elastic members 24 in an illustrated example. However, for example, another elongated elastic member such as flat rubber may be used.

As another mode, although not illustrated, an appropriate modification may be made such that the elastic film stretchable structure 20X may not be provided in the intermediate portion L between the lower torso portion T of the front body F and the lower torso portion T of the back body B, the stretchable structure 20X may be continuously provided in the front-back direction LD from the inside of the lower torso portion T of the front body F to the inside of the lower torso portion T of the back body B through the intermediate portion L, or the elastic film stretchable structure 20X may be provided only in any one of the front body F and the back body B.

Figure 8:
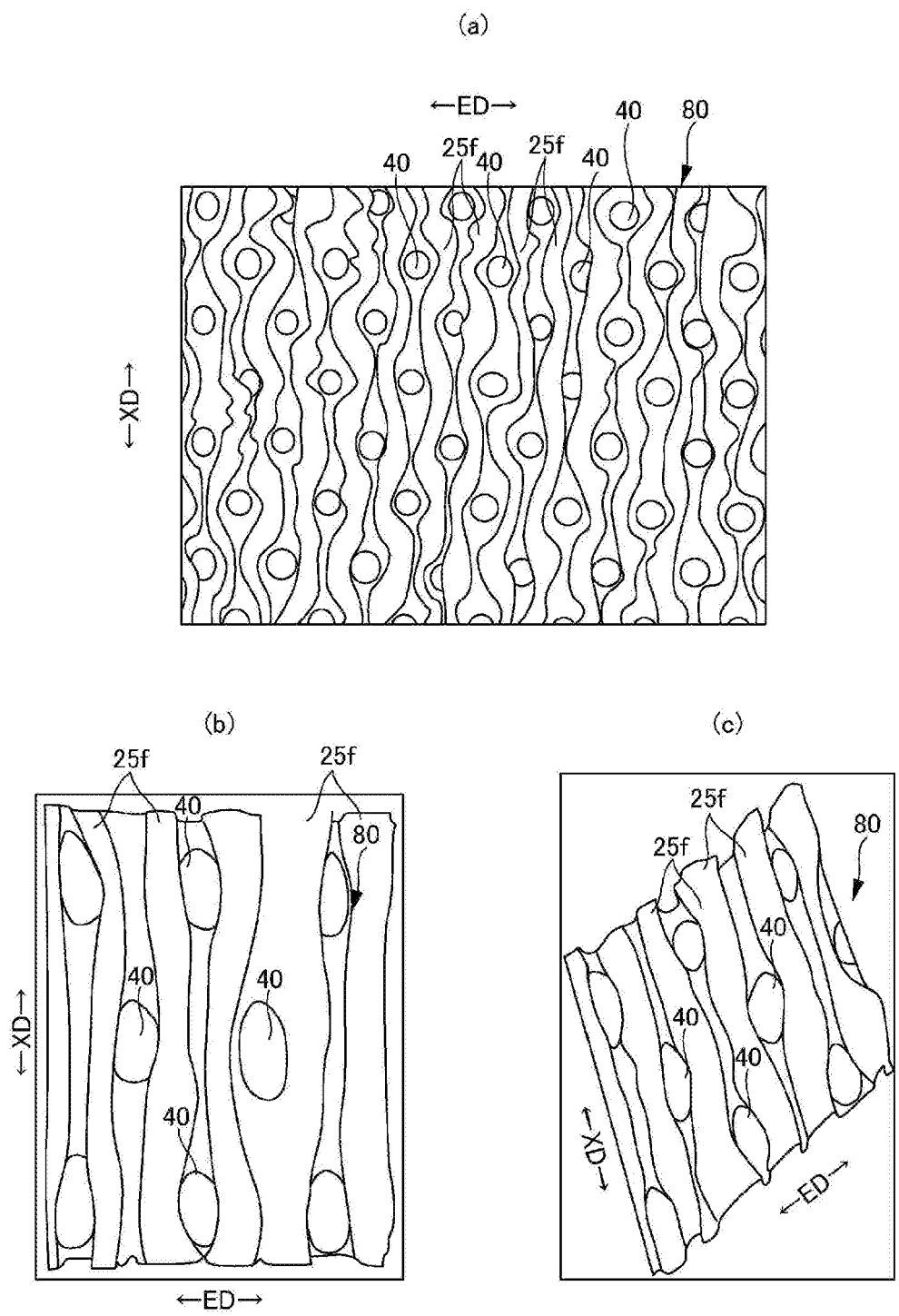
FIG. 8(a) is a trace diagram of a microscope photograph from a plane direction.
FIG. 8(b) is a trace diagram of a high-magnification microscope photograph from the plane direction.
FIG. 8(c) is a trace diagram of a high-magnification microscope photograph from an oblique direction in a stretchable region of a sample.

A shape of each of the sheet bonded portions 40 and a shape of each of the through-holes 31 in a natural length state may be appropriately determined. However, it is possible to adopt an arbitrary shape such as a perfect circle (see FIG. 7 and FIG. 8), an ellipse, a polygon such as a triangle, a rectangle (see FIG. 9 to FIG. 12), a rhombus (see FIG. 13(*b*)), etc., a convex lens shape (see FIG. 13(*a*)), a concave lens shape (see FIG. 14(*a*)), a star shape, a cloud shape, etc. The dimensions of each of the sheet bonded portions are not particularly restricted. However, a maximum length 40*y* is preferably set to 0.5 to 3.0 mm, particularly 0.7 to 1.1 mm, and a maximum width 40*x* is preferably set to 0.1 to 3.0 mm, particularly 0.1 to 1.1 mm in a case of a shape which is long in an orthogonal direction XD orthogonal to the stretchable direction ED.

A size of each of the sheet bonded portions 40 may be appropriately determined. However, when the size is excessively large, the hardness of the sheet bonded portions 40 has a significant influence on touch. When the size is excessively small, a bonded area is small, and materials may not be sufficiently attached to each other. Thus, in general, an area of each of the sheet bonded portions 40 is preferably set to about 0.14 to 3.5 mm$^2$. An area of an opening of each of the through-holes 31 may be greater than or equal to that of each of the sheet bonded portions since the sheet bonded portions are formed via the through-holes 31, and the area is preferably set to about 1 to 1.5 times the area of each of the sheet bonded portions. The area of the opening of each of the through-holes 31 refers to a value in a natural length state and in a state where the elastic film 30, the first sheet layer 20A and the second sheet layer 20B are provided in one unit, not in a state of the elastic film 30 alone, and refers to a minimum value in a case in which the area of the opening of each of the through-holes 31 is not uniform in a thickness direction such as a case in which the area is different between a front and a back of the elastic film 30.

Figure 21:
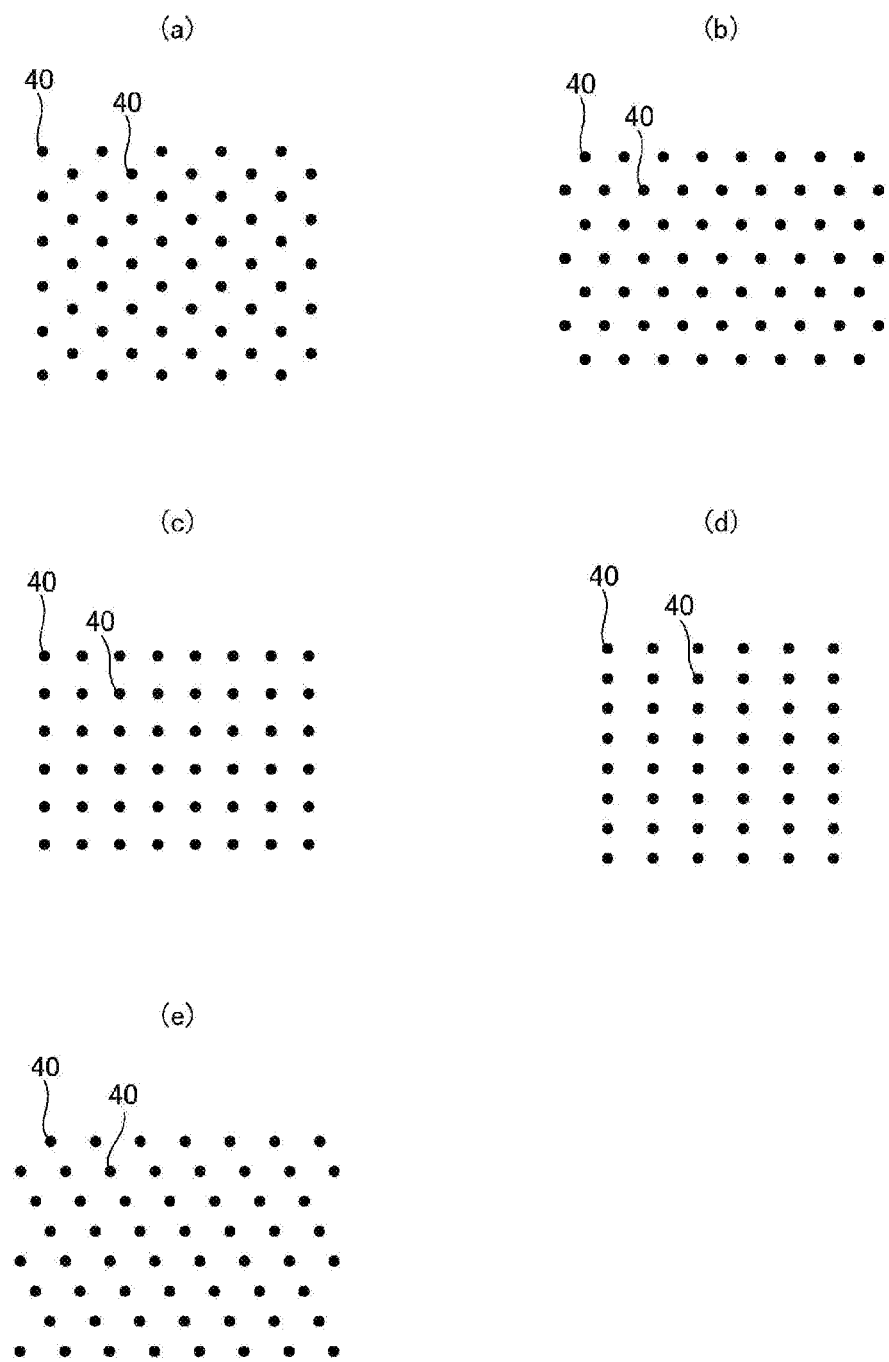
FIG. 21 is a plan view illustrating various arrangement examples of the sheet bonded portions.

The planar geometries of the sheet bonded portions 40 and the through-holes 31 may be appropriately determined. However, it is preferable to adopt a planar array in which the sheet bonded portions 40 and the through-holes 31 are regularly repeated, such as an oblique lattice shape illustrated in FIG. 21(*a*), a hexagonal lattice shape (also referred to as a staggered lattice) illustrated in FIG. 21(*b*), a square lattice shape illustrated in FIG. 21(*c*), a rectangular lattice shape illustrated in FIG. 21(*d*), a parallelotope lattice shape illustrated in FIG. 21(*e*) (a mode in which two groups are provided such that a large number of parallel oblique row groups intersect each other, as shown in the drawings), etc. (including a mode in which these shapes are inclined at an angle less than 90 degrees with respect to the stretchable direction ED). Additionally, it is also possible to adopt a planar array in which a group of the sheet bonded portions 40 (arrangement of each group may be regular or irregular, and a pattern, a letter shape, etc. may be used) is regularly repeated.

The first sheet layer 20A and the second sheet layer 20B are bonded in the sheet bonded portions 40 via the through-holes 31 formed in the elastic film 30. In this case, it is desirable that neither the first sheet layer 20A nor the second sheet layer 20B is bonded to the elastic film 30 at least in a portion other than a portion between the first sheet layer 20A and the second sheet layer 20B in the sheet bonded portions 40.

Ultrasonic welding is desirable as bonding means of the first sheet layer 20A and the second sheet layer 20B in the sheet bonded portions 40 in that the first sheet layer 20A and the second sheet layer 20B do not become hard.

Figure 17:
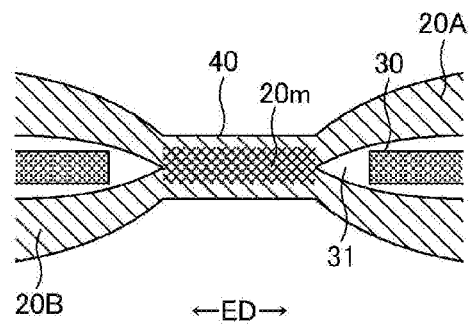
FIG. 17 is a cross-sectional view schematically illustrating a cross section of a main part of an outer member stretched to a certain extent.
Figure 17:
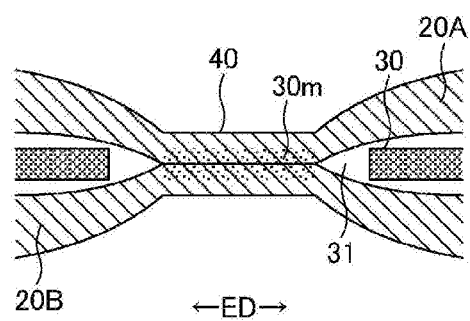
Figure 17:
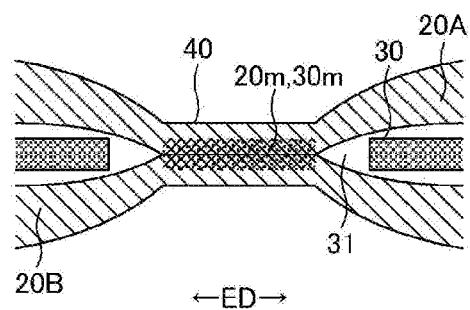
Figure 19:
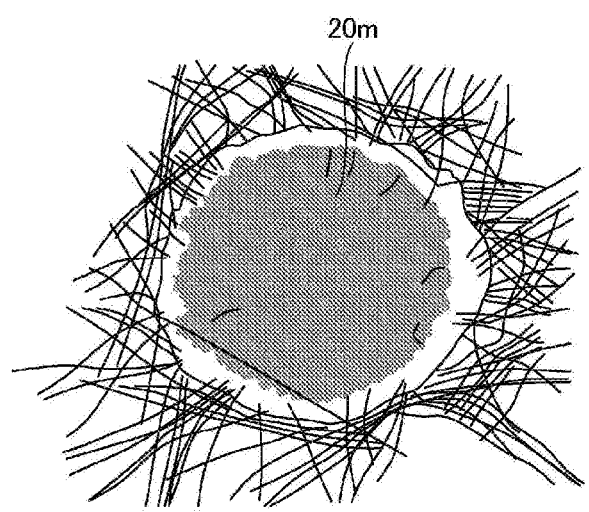
FIG. 19(a) is a trace diagram of a plan photograph of sheet bonded portions formed in a first welding mode.
FIG. 19(b) is a trace diagram of a plan photograph of the sheet bonded portions formed in a third welding mode.
Figure 19:
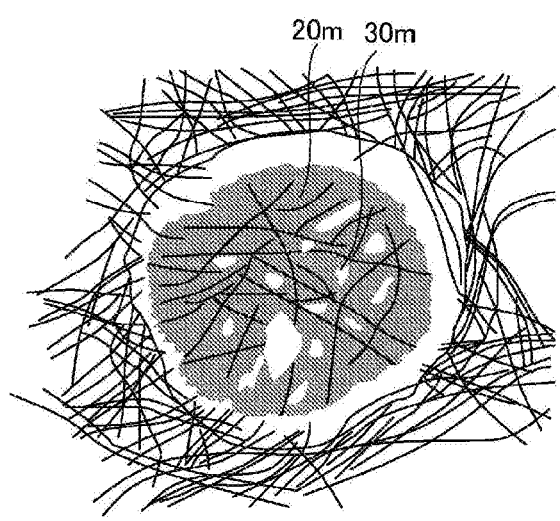

As a mode in which the sheet bonded portions 40 are formed by material welding, it is possible to adopt anyone of a first welding mode (see FIG. 17(*a*)) in which the first sheet layer 20A and the second sheet layer 20B are bonded only by a melted and solidified material 20*m* corresponding to a most part or a part of at least one of the first sheet layer 20A and the second sheet layer 20B in the sheet bonded portions 40; a second welding mode (see FIG. 17(*b*)) in which the first sheet layer 20A and the second sheet layer 20B are bonded only by a melted and solidified material 30*m* corresponding to a whole, a most part, or a part of the elastic film 30 in the sheet bonded portions 40; and a third welding mode (see FIG. 17(c)) obtained by combining these welding modes, and it is preferable to adopt the second and third welding modes. A particularly preferable mode is a mode in which the first sheet layer 20A and the second sheet layer 20B are bonded by the melted and solidified material 20m corresponding to a part of the first sheet layer 20A and the second sheet layer 20B and the melted and solidified material 30m corresponding to a whole or a most part of the elastic film 30 in the sheet bonded portions 40. The melted and solidified material 30m of the elastic film 30 is seen in the melted and solidified material 20m with the fibers of the first sheet layer 20A or the second sheet layer 20B in the third welding mode illustrated in FIG. 19(b), however, the melted and solidified material of the elastic film is hardly seen in the melted and solidified material 20m with the fibers of the first sheet layer 20A or the second sheet layer 20B in the first welding mode illustrated in FIG. 19(a).

In a case in which the first sheet layer 20A and the second sheet layer 20B are bonded using the melted and solidified material 20m corresponding to a most part or a part of at least one of the first sheet layer 20A and the second sheet layer 20B as an adhesive as in the first welding mode or the third welding mode, it is preferable that a part of the first sheet layer 20A and the second sheet layer 20B is not melted in order not to harden the sheet bonded portions 40. When the first sheet layer 20A and the second sheet layer 20B are nonwoven fabrics, a case in which a part of the first sheet layer 20A and the second sheet layer 20B is not melted includes a mode in which for all fibers of the sheet bonded portions 40, a core (including a central portion of each component fiber of a conjugate fiber in addition to a core of the conjugate fiber) remains while a surrounding portion (including a portion on a surface layer side of each component fiber of a conjugate fiber in addition to a sheath in the conjugate fiber) melts; a mode in which some fibers do not melt at all while all remaining fibers melt; or a mode in which a core remains while a surrounding portion melts.

Peel strength becomes high when the first sheet layer 20A and the second sheet layer 20B are bonded using the melted and solidified material 30m of the elastic film 30 as an adhesive as in the second welding mode and the third welding mode. In the second welding mode, under the condition that a melting point of at least one of the first sheet layer 20A and the second sheet layer 20B is higher than a melting point of the elastic film 30 and a heating temperature at the time of forming the sheet bonded portions 40, the elastic film 30 may be interposed between the first sheet layer 20A and the second sheet layer 20B, portions to be the sheet bonded portions 40 may be pressed and heated, and only the elastic film 30 may be melted, thereby performing manufacture. Meanwhile, in the third welding mode, under the condition that a melting point of at least one of the first sheet layer 20A and the second sheet layer 20B is higher than the melting point of the elastic film 30, the elastic film 30 may be interposed between the first sheet layer 20A and the second sheet layer 20B, the portions to be the sheet bonded portions 40 may be pressed and heated, and at least one of the first sheet layer 20A and the second sheet layer 20B and the elastic film 30 may be melted to perform the welding. From this point of view, the melting point of the elastic film 30 is preferably about 80 to 145° C., melting points of the first sheet layer 20A and the second sheet layer 20B are preferably about 85 to 190° C., particularly, 150 to 190° C., and a difference between the melting points of the first sheet layer 20A and the second sheet layer 20B and the melting point of the elastic film 30 is preferably about 60 to 90° C., particularly about 60 to 80° C. In addition, the heating temperature is preferably set to 100 to 150° C.

Figure 18:
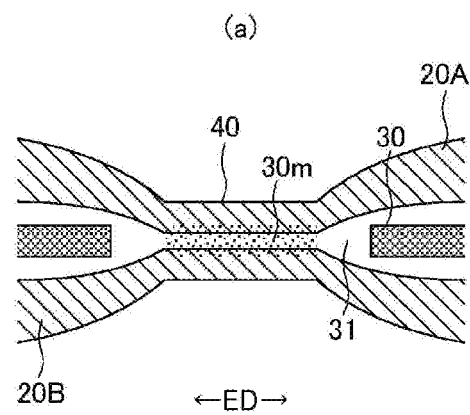
FIG. 18 is a cross-sectional view schematically illustrating a cross section of the main part of the outer member stretched to a certain extent.
Figure 18:
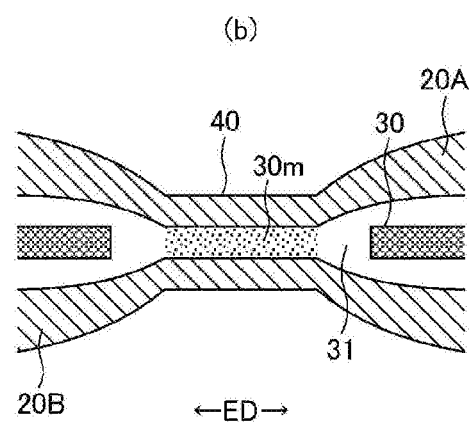
Figure 18:
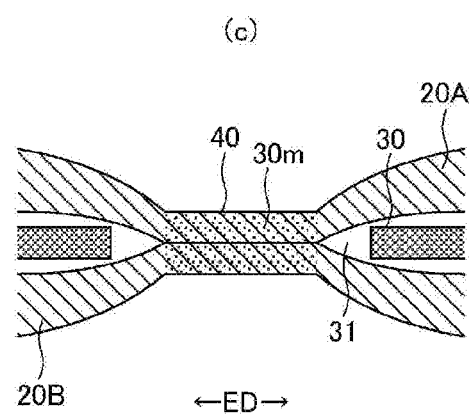

In the second welding mode and the third welding mode, when the first sheet layer 20A and the second sheet layer 20B are nonwoven fabric, the melted and solidified material 30m of the elastic film 30 may infiltrate among fibers throughout the whole thickness direction of the first sheet layer 20A and the second sheet layer 20B of the sheet bonded portions 40 as illustrated in FIG. 18(c). However, flexibility of the sheet bonded portions 40 becomes high in a mode in which the melted and solidified material 30m infiltrates among fibers in the thickness direction halfway as illustrated in FIGS. 17(b), 17(c), and FIG. 18(a), or a mode in which the melted and solidified material 30m hardly infiltrates among the fibers of the first sheet layer 20A and the second sheet layer 20B as illustrated in FIG. 18(b).

Figure 20:
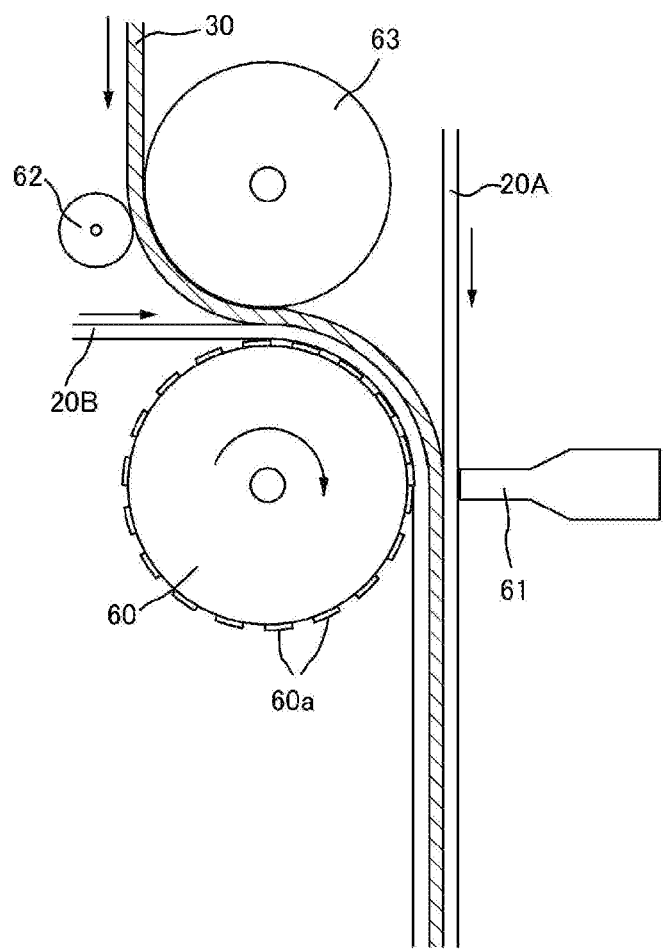
FIG. 20 is a schematic view of an ultrasonic sealing device.

FIG. 20 illustrates an example of an ultrasonic sealing device suitable for forming the second welding mode and the third welding mode. In this ultrasonic sealing device, to form bond portions 40, the first sheet layer 20A, the elastic film 30, and the second sheet layer 20B are fed between an ultrasonic horn 61 and an anvil roll 60 having a pattern of protrusions 60a of the sheet bonded portions 40 on an external surface. In this instance, for example, when a feed speed of conveyance of the elastic film 30 at an upstream side by a feed drive roll 63 and a nip roll 62 is controlled to be lower than a feed speed of conveyance after the anvil roll 60 and the ultrasonic horn 61, the elastic film 30 is stretched to a predetermined stretch rate in an MD (machine direction, flow direction) on a path from a nip position by the feed drive roll 63 and the nip roll 62 to a sealing position by the anvil roll 60 and the ultrasonic horn 61. A stretch rate of the elastic film 30 may be set by selecting a speed difference between the anvil roll 60 and the feed drive roll 63, and may be set to, for example, about 300% to 500% (three to five times). Reference symbol 62 denotes the nip roll. The first sheet layer 20A, the elastic film 30, and the second sheet layer 20B fed between the anvil roll 60 and the ultrasonic horn 61 are, in a stacked state in this order, heated by ultrasonic vibration energy of the ultrasonic horn 61 while being pressed between the protrusions 60a and the ultrasonic horn 61. Further, the through-holes 31 are formed in the elastic film 30 by melting only the elastic film 30 or melting the elastic film 30 and at least one of the first sheet layer 20A and the second sheet layer 20B. At the same time, the first sheet layer 20A and the second sheet layer 20B are bonded through the through-holes 31. Therefore, in this case, an area rate of the sheet bonded portions 40 may be selected by selecting a size, a shape, and arrangement (an interval between a roll length direction QD and a roll circumferential direction RD) of the protrusions 60a of the anvil roll 60.

Figure 9:
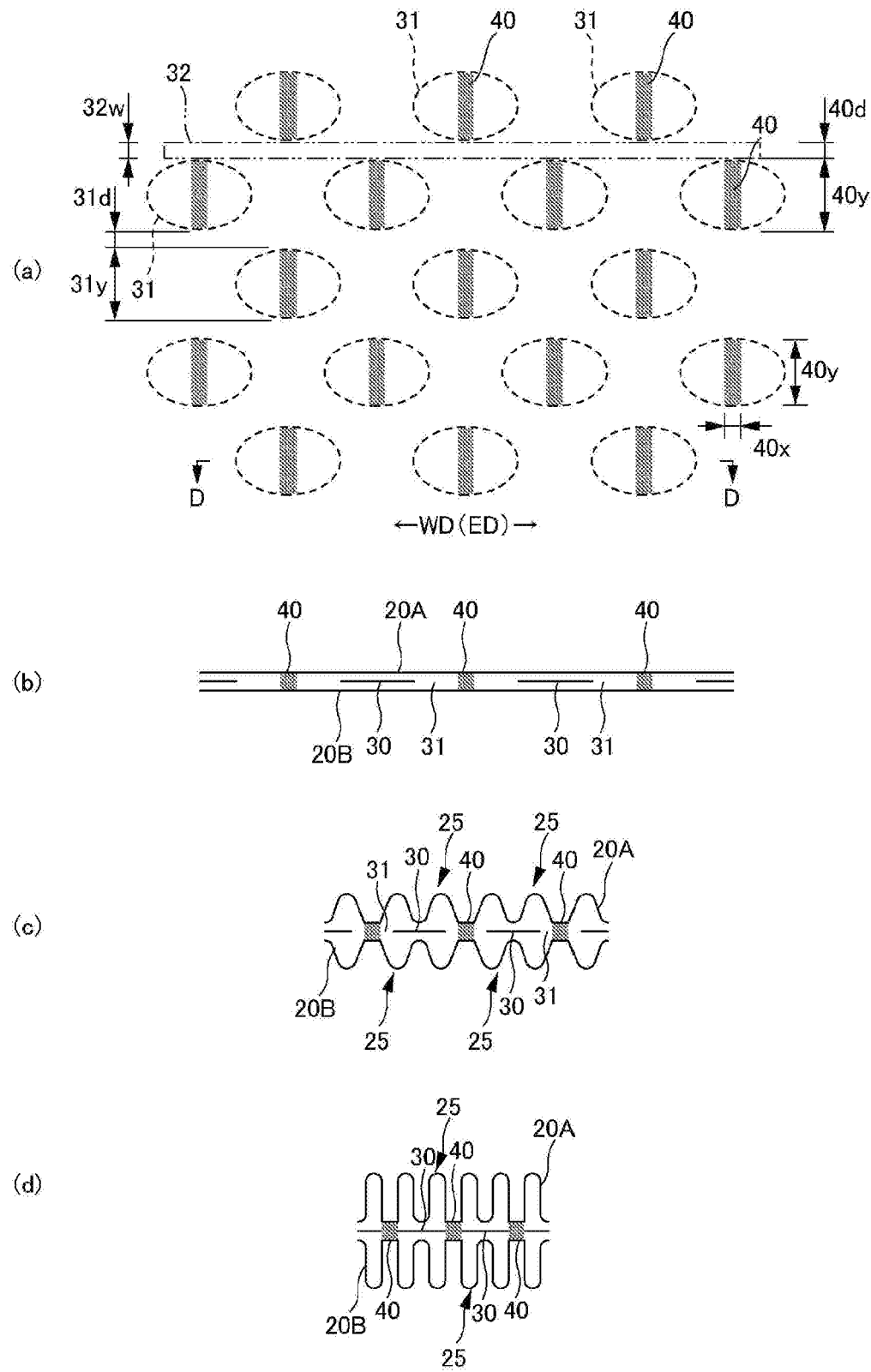
FIG. 9(a) is a plan view of the main part of the stretchable region.
FIG. 9(b) is a D-D cross-sectional view of FIG. 9(a)
FIG. 9(c) is a cross-sectional view in a worn state.
FIG. 9(d) is a cross-sectional view in a natural length state.
Figure 10:
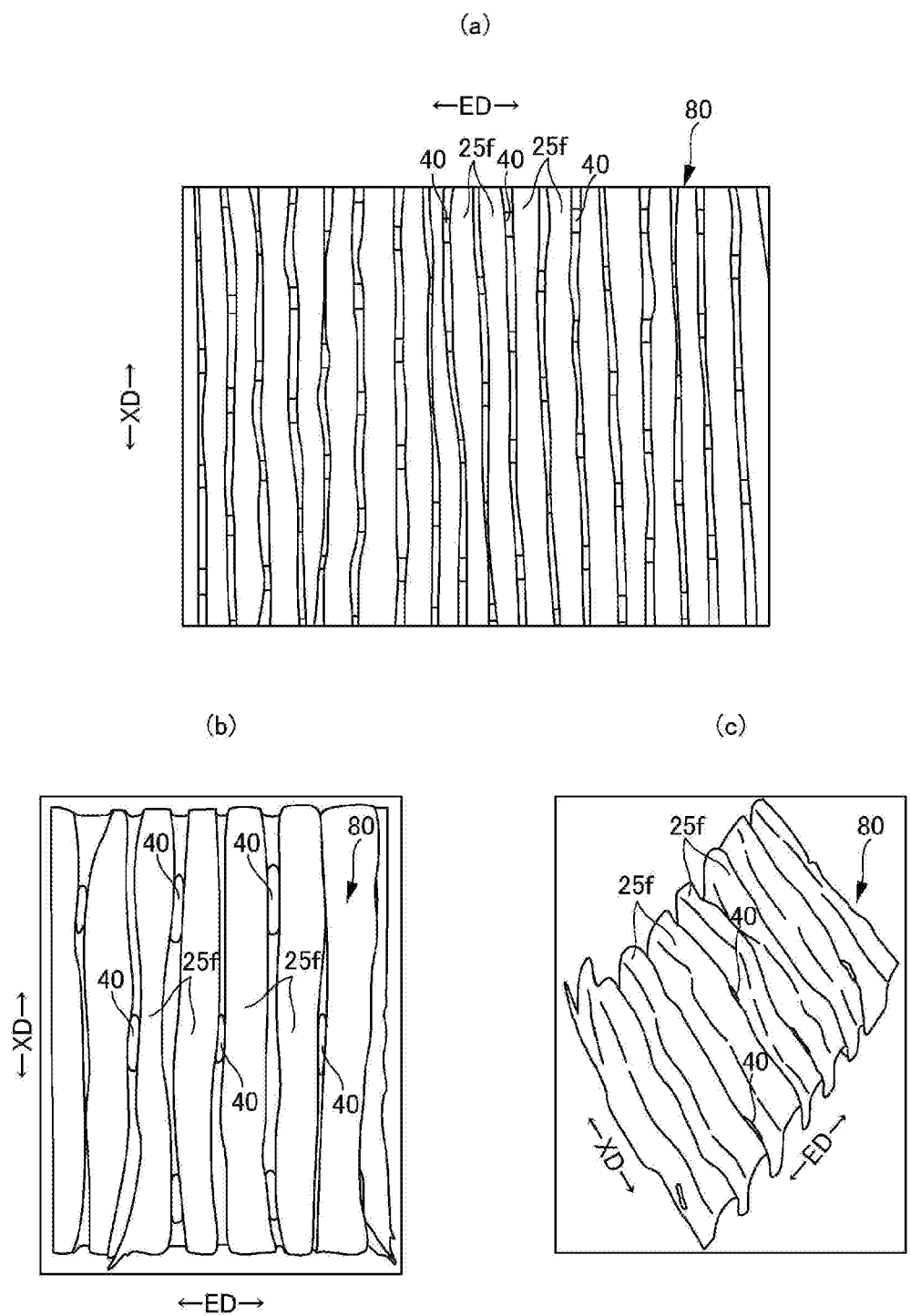
FIG. 10(a) is a trace diagram of a microscope photograph from the plane direction.
FIG. 10(b) is a trace diagram of a high-magnification microscope photograph from the plane direction.
FIG. 10(c) is a trace diagram of a high-magnification microscope photograph from the oblique direction in the stretchable region of the sample.
Figure 11:
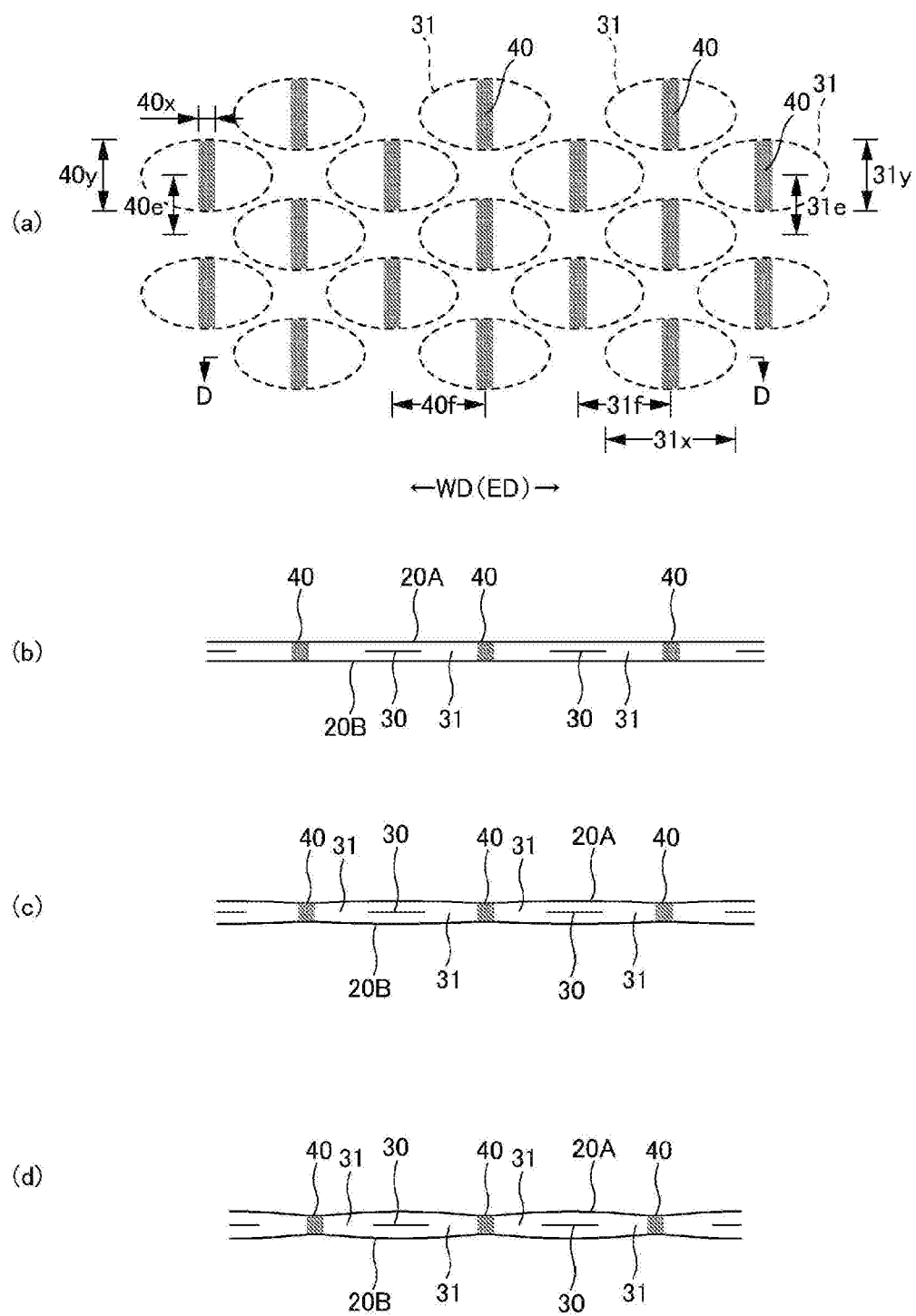
FIG. 11(a) is a plan view of a main part of a non-stretchable region.
FIG. 11(b) is a D-D cross-sectional view of FIG. 11(a)
FIG. 11(c) is a cross-sectional view in a worn state.
FIG. 11(d) is a cross-sectional view in a natural length state.

Although the reason for formation of the through-holes 31 is not necessarily clear, it is considered that openings are formed by melting the elastic film 30 at portions corresponding to the protrusions 60a of the anvil roll 60 so as to be removed from the surroundings. In this instance, a portion between two adjacent through-holes 31 arranged in the stretchable direction ED in the elastic film 30 is cut at both sides thereof in the stretchable direction ED by the through-holes 31 as illustrated in FIG. 7(a), FIG. 9(a), and FIG. 11(a), and supports at both sides in a contraction direction are lost. Thus, within an extent that continuity in the orthogonal direction XD can be maintained, the closer to the central side in the orthogonal direction XD, the more the elastic film 30 contracts to the central side in the stretchable direction ED to be commensurable so that the through-holes 31 are enlarged in the stretchable direction ED. When the sheet bonded portions 40 are formed in a pattern with sections being left in which the elastic film 30 linearly continues along the stretchable direction ED, as in a stretchable region 80 explained after, and when the elastic film 30 contracts to the natural length state for example by cutting for obtaining individual products, enlarged portions of each through-hole 31 contract in the stretchable direction ED so that gaps cannot be formed between each through-hole 31 and each sheet bonded portion 40 as illustrated in FIG. 7(*a*) and FIG. 9(*a*). On the other hand, when the sheet bonded portions 40 are formed in a pattern without such sections in which the elastic film 30 linearly continues along the stretchable direction ED, as in a non-stretchable region 70 explained after, even if the elastic film 30 is cut for obtaining the individual products, contraction is not substantially performed, as illustrated in FIG. 11(*a*). Thus, large gaps are left between each through-hole 31 and each sheet bonded portion 40.

Constituent materials of the first sheet layer 20A and the second sheet layer 20B are not particularly limited as long as the materials have sheet shapes, and nonwoven fabric is preferably used in view of air permeability and flexibility. The nonwoven fabric may be composed of any raw fiber. Examples of the raw fiber include synthetic fibers, such as olefin fibers, e.g., polyethylene fibers and polypropylene fibers, polyester fibers, and polyamide fibers; recycled fibers, such as rayon and cupra; natural fibers, such as cotton; and blend or conjugate fibers composed of two or more of these fibers. The nonwoven fabric may be prepared by any process. Examples of such a process include well-known processes, such as spun lacing, spun bonding, thermal bonding, melt blowing, needle punching, air-through processes, and point bonding. The nonwoven fabric preferably has a basis weight of approximately 12 to approximately 20 g/m$^2$. The first sheet layer 20A and the second sheet layer 20B may be composed of a pair of facing layers prepared by folding back a single sheet that is partially or entirely folded back. For example, as in the illustrated mode, in the waist region 23, a component located outer side may be used as the second sheet layer 20B, the folded part 20C formed by folding back to the internal surface side at the waist opening edge thereof may be used as the first sheet layer 20A, and the elastic film 30 may be interposed therebetween, and in the rest part, a component located inner side may be used as the first sheet layer 20A, another component located outer side may be used as the second sheet layer 20B, and the elastic film 30 may be interposed therebetween. The component of the first sheet layer 20A and the component of the second sheet layer 20B may be separately provided throughout the whole part in the front-back direction LD, and the elastic film 30 may be interposed between the component of the first sheet layer 20A and the component of the second sheet layer 20B without folding back the component members.

The elastic film 30 may be composed of any thermoplastic resin film having elasticity. For example, it is possible to use a film in which a large number of holes or slits are formed for ventilation in addition to a non-porous film. In particular, it is preferable when the elastic film 30 has a tensile strength in the width direction WD (the stretchable direction ED, the MD) of 8 to 25 N/35 mm, tensile strength in the front-back direction LD (the orthogonal direction XD, the CD) of 5 to 20 N/35 mm, tensile elongation in the width direction WD of 450 to 1,050%, and tensile elongation in the front-back direction LD of 450 to 1,400%. The thickness of the elastic film 30 is not particularly restricted. However, the thickness is preferably in a range of about 20 to 40 μm.

(Stretchable Region)

A region having the elastic film stretchable structure 20X in the outer member 20 has a stretchable region which is stretchable in the width direction WD. The stretchable region 80 has sections 32 in which the elastic film 30 linearly continues along the width direction WD. The stretchable region contracted in the width direction WD by a contraction force of the elastic film 30 is extensible in the width direction WD. More specifically, in a state in which the elastic film 30 is stretched in the width direction WD, the first sheet layer 20A and the second sheet layer 20B are bonded via the through-holes 31 of the elastic film 30 at intervals in the width direction WD and the front-back direction LD orthogonal thereto (the orthogonal direction XD), and the large number of sheet bonded portions 40 are formed, thereby forming the entire elastic film stretchable structure 20X. Further, in the stretchable region 80, it is possible to impart elasticity by arranging the through-holes 31 such that the stretchable region 80 has the sections in which the elastic film 30 linearly continues along the width direction WD.

In the stretchable region 80, in the natural length state, as illustrated in FIG. 7(*d*) and FIG. 9(*d*), the first sheet layer 20A and the second sheet layer 20B between the two adjacent sheet bonded portions 40 are raised in directions away from each other, and thus a contraction wrinkle 25 extending in the front-back direction LD is formed. Further, as illustrated in FIG. 7(*c*) and FIG. 9(*c*), even in a worn state stretched to some extent in the width direction WD, the contraction wrinkles 25 are still remained while being stretched. In addition, as in the illustrated mode, when neither the first sheet layer 20A nor the second sheet layer 20B is bonded to the elastic film 30 at least in a portion other than a portion between the first sheet layer 20A and the second sheet layer 20B in the sheet bonded portions 40, as is understood from FIG. 7(*c*) and FIG. 9(*c*) assuming the worn state and FIGS. 7(*a*) and 7(*b*) and FIGS. 9(*a*) and 9(*b*) assuming the spread state of the first sheet layer 20A and the second sheet layer 20B, the gaps are formed between each through-hole 31 in the elastic film 30 and each sheet bonded portion 40 and in these states, air permeability is imparted by these gaps even when the material of the elastic film 30 is a non-porous film or a non-porous sheet. In addition, in the natural length state illustrated in FIG. 7(*d*) and FIG. 9(*d*), the through-holes 31 are narrowed due to contraction of the elastic film 30, and the gaps are hardly formed between the through-hole 31 and the sheet bonded portion 40. States of the contraction wrinkle 25 in the worn state and the natural length state are shown in also trace diagrams of sample photographs of FIG. 8 and FIG. 10.

It is desirable that an elongation at an elastic limit of the stretchable region 80 in the width direction WD is set to 200% or more (preferably 265% to 295%). The elongation at the elastic limit of the stretchable region 80 is substantially determined by the stretch rate of the elastic film 30 in the manufacturing. However, the elongation at the elastic limit decreases due to a factor that inhibits contraction in the width direction WD based thereon. A main inhibition factor corresponds to a ratio of the length 40*x* of the sheet bonded portions 40 to a unit length in the width direction WD. As this ratio increases, the elongation at the elastic limit decreases. In general, since the length 40*x* of each of the sheet bonded portions 40 correlates with the area rate of the sheet bonded portions 40, the elongation at the elastic limit of the stretchable region 80 may be adjusted by the area rate of the sheet bonded portions 40.

Stretching stress of the stretchable region 80 may be adjusted mainly by a sum of widths 32w of the sections 32 in which the elastic film 30 linearly continues along the width direction WD. The width 32w of the section 32 in which the elastic film 30 linearly continues along the width direction WD is equal to an interval 31d of the two adjacent through-holes 31 in the front-back direction LD coming into contact with both side edges of the continuing section 32. The interval 31d of the two adjacent through-holes 31 is equal to an interval 40d of the two adjacent sheet bonded portions 40 in the front-back direction LD coming into contact with the both side edges of the continuing section in the front-back direction LD, when the length 31y of the through-hole 31 in the front-back direction LD is equal to the length 40y of the sheet bonded portion 40 in the front-back direction LD (for example, when a scheme of simultaneously forming the through-holes 31 and the sheet bonded portions 40 described above is adopted). Therefore, in this case, the stretching stress of the stretchable region 80 may be adjusted by a ratio of the length 40y of each of the sheet bonded portions 40 to a unit length in the front-back direction LD. In general, since the length 40y of each of the sheet bonded portions 40 correlates with the area rate of the sheet bonded portions 40, the stretching stress of the stretchable region 80 may be adjusted by the area rate of the sheet bonded portions 40. The stretching stress in stretching to 50% of an elastic limit may be estimated as the stretching stress of the stretchable region 80.

The area rate of the sheet bonded portions 40 and the area of each of the sheet bonded portions 40 in the stretchable region 80 may be appropriately determined. However, in general, the area rate and the areas are preferably set within the following ranges.

Area of each of sheet bonded portions 40: 0.14 to 3.5 mm² (particularly 0.14 to 1.0 mm²)

Area rate of sheet bonded portions 40: 1.8 to 19.1% (particularly 1.8 to 10.6%)

As described above, the elongation at the elastic limit and the stretching stress of the stretchable region 80 may be adjusted by the area of each of the sheet bonded portions 40. Thus, as illustrated in FIG. 15, it is possible to provide a plurality of regions having different area rates of the sheet bonded portions 40 in the stretchable region 80, and to change fitting according to the sites. In a mode illustrated in FIG. 15, in the front body F, regions 81, each of which is extending in an oblique direction along a groin, and edge portion regions 82 of the leg openings have, when compared to other regions, higher area rates of the sheet bonded portions 40, and thus have smaller stretching stresses, resulting in abilities to stretch flexibly. In addition, in the back body B, ilium facing regions 83 and the edge portion regions 82 of the leg openings have, when compared to other regions, higher area rates of the sheet bonded portions 40, and thus have smaller stretching stresses, resulting in abilities to stretch flexibly.

(Non-Stretchable Region)

In a region having the elastic film stretchable structure 20X in the outer member 20, as illustrated in FIG. 15, it is possible to provide the non-stretchable region 70. Arrangement of the stretchable region 80 and the non-stretchable region 70 may be appropriately determined. In the case of the outer member 20 of the underpants-type disposable diaper as in the present embodiment, a portion overlapping with the absorber 13 is a region unnecessary to stretch and contract. Thus, as in the illustrated mode, a part or a whole of the portion overlapping the absorber 13 (it is desirable to include substantially the entire internal and external fixed region 10B) is preferably set to the non-stretchable region 70. It is as a matter of course possible to provide the non-stretchable region 70 from the region overlapping the absorber 13 to a region not overlapping the absorber 13 located in the width direction WD or the front-back direction LD thereof, or it is possible to provide the non-stretchable region 70 only in the region not overlapping the absorber 13.

The non-stretchable region 70 is configured, even though the elastic film 30 continues in the width direction WD, so as not to have a part in which the elastic film 30 linearly continues along the width direction WD, due to the presence of the through-holes 31. Therefore, even though the elastic film stretchable structure 20X is configured as a whole to include both the stretchable region 80 and the non-stretchable region 70 by bonding the first sheet layer 20A and the second sheet layer 20B through the through-holes 31 of the elastic film 30 to form the large number of sheet bonded portions 40 at intervals in the width direction WD and the front-back direction LD orthogonal thereto while the elastic film 30 is stretched in the width direction WD, in the non-stretchable region 70, the elastic film 30 does not linearly continue along the width direction WD as illustrated in FIG. 11. Thus, the contraction force of the elastic film 30 hardly acts on the first sheet layer 20A and the second sheet layer 20B, elasticity is almost lost, and the elongation at the elastic limit approaches 100%. Further, in the non-stretchable region 70, the first sheet layer 20A and the second sheet layer 20B are bonded by the large number of sheet bonded portions 40 arranged at intervals, and the sheet bonded portions 40 are discontinuous. Thus, a decrease in flexibility is prevented. In other words, it is possible to form the stretchable region 80 and the non-stretchable region 70 depending on the presence or absence of the part in which the elastic film 30 does not linearly continue along the width direction WD. In addition, continuity of the elastic film 30 still remains in the non-stretchable region 70. As understood from a trace diagram of a sample photograph illustrated in FIG. 12, since an independent cut piece of the elastic film 30 is not left, and no wrinkle is formed, appearance is extremely excellent, and air permeability in the thickness direction by the through-holes 31 is ensured. In the non-stretchable region 70, the elongation at the elastic limit in the width direction WD is preferably 120% or less (preferably 110% or less, more preferably 1000).

Figure 12:
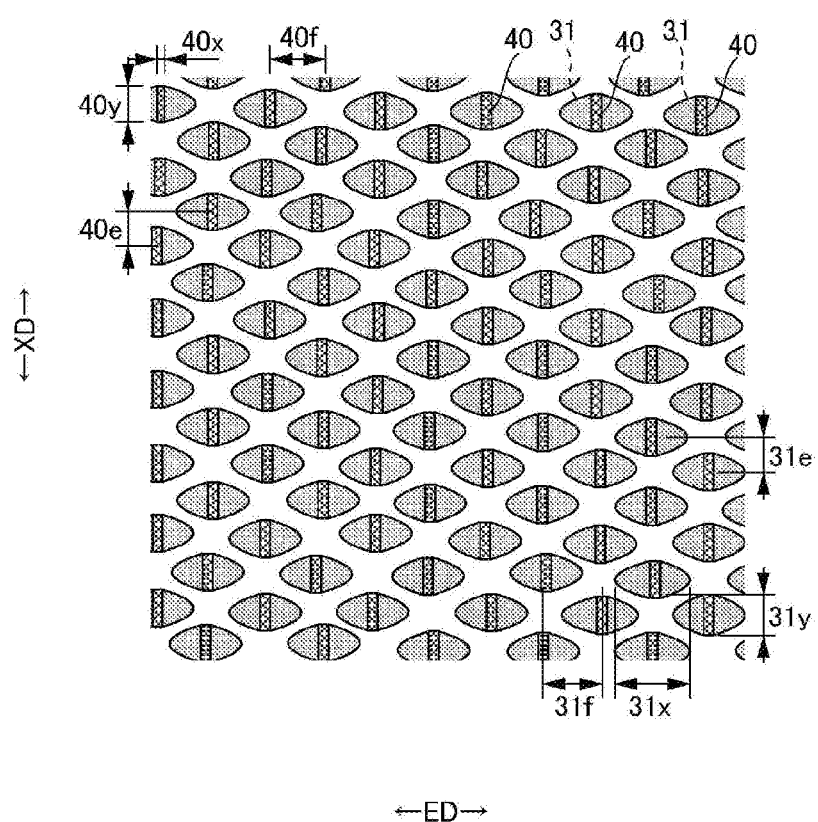
FIG. 12 is a trace diagram of a photograph of a non-stretchable region of a sample.
Figure 13:
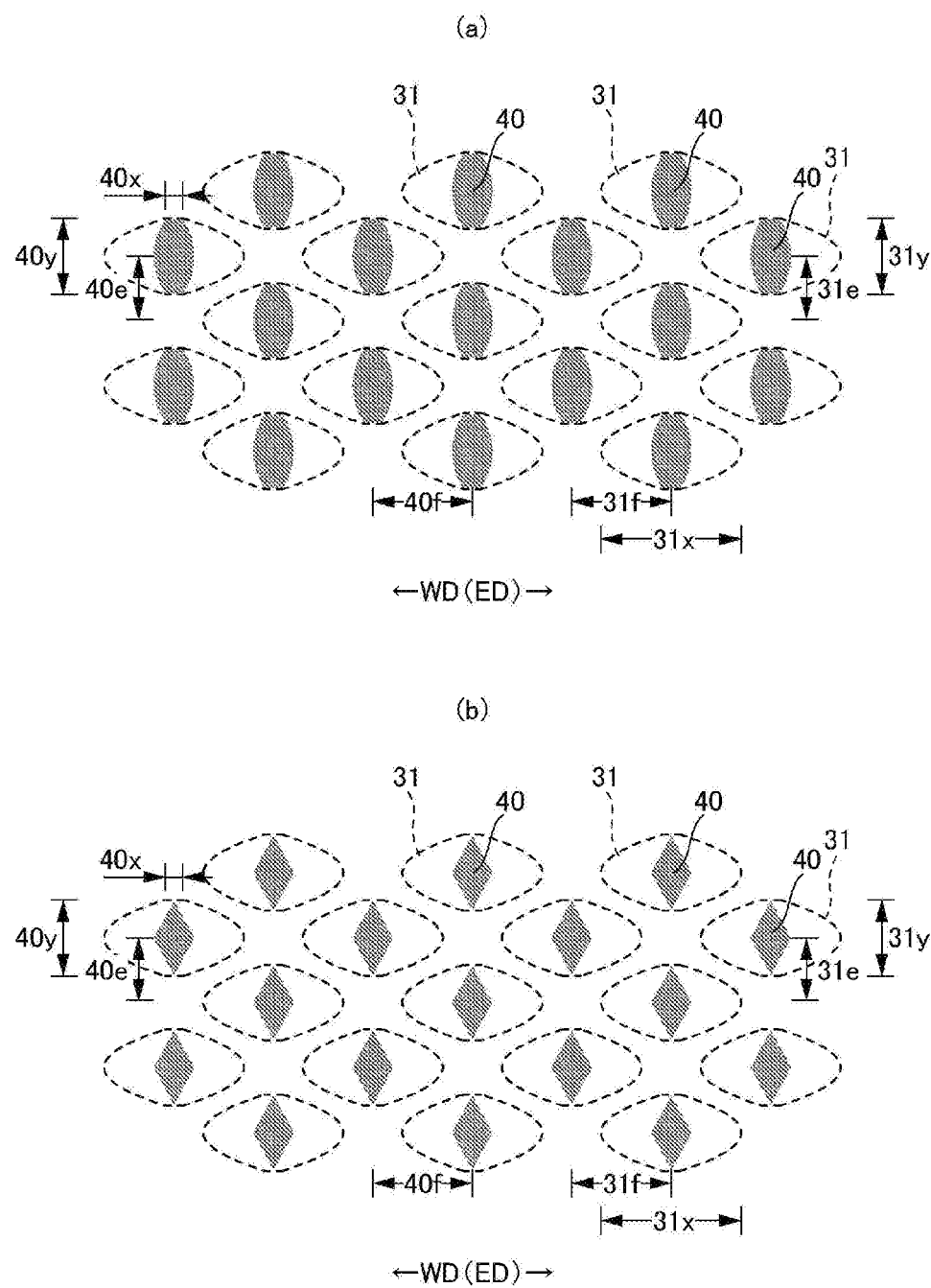
FIG. 13 is a plan view of a main part of the non-stretchable region.
Figure 14:
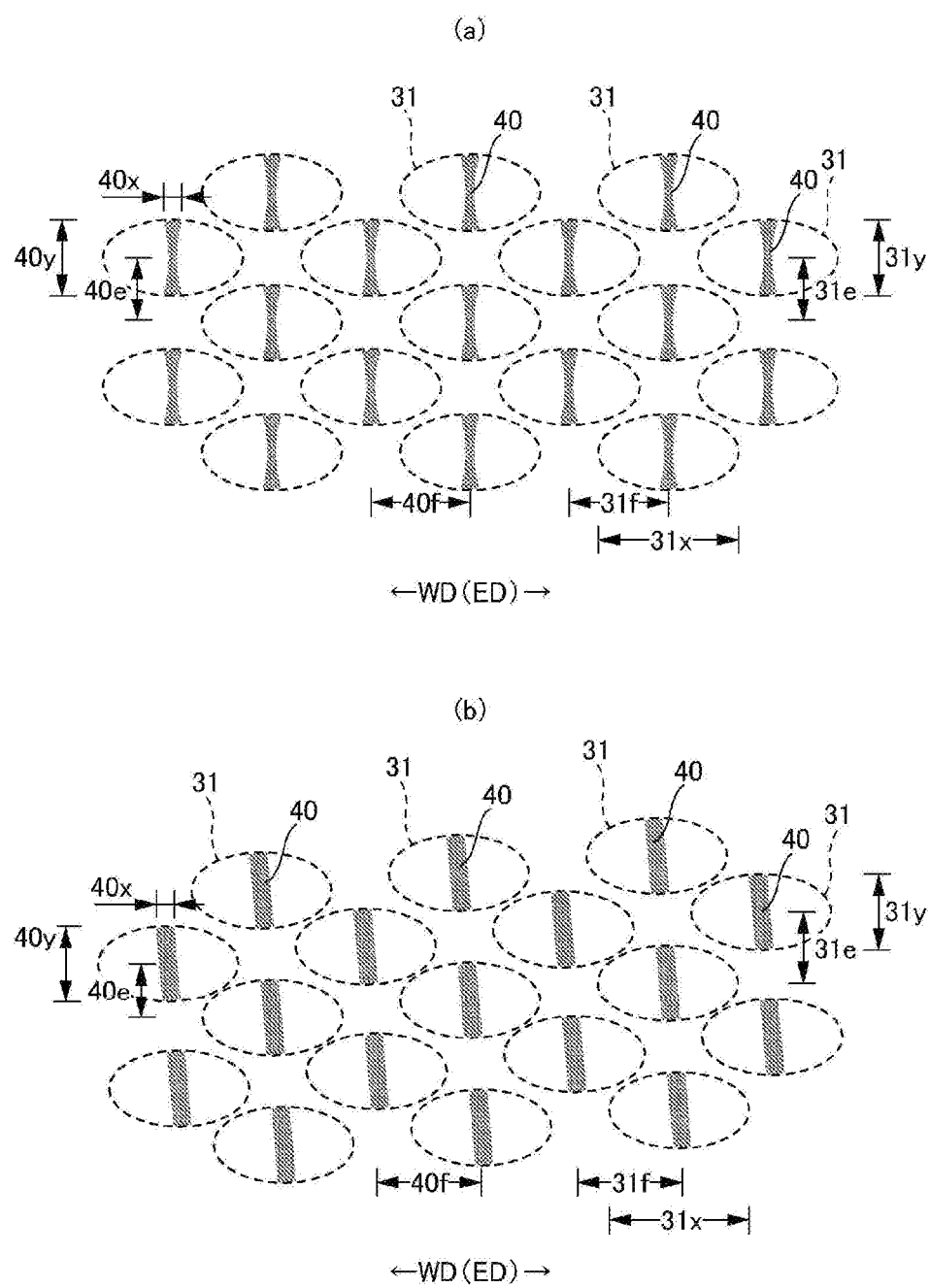
FIG. 14 is a plan view of the main part of the non-stretchable region.

An arrangement pattern of the through-holes 31 in the elastic film 30 in the non-stretchable region 70 may be appropriately determined. However, when staggered arrangement is adopted as illustrated in FIG. 11 to FIG. 14, and a pattern in which a center-to-center interval 31e of the two adjacent through-holes 31 in the front-back direction LD is shorter than the length 31y of each of the through-holes 31 in the front-back direction LD is adopted, linear continuity in the width direction WD may be almost completely eliminated while maintaining continuity of the elastic film 30, and appearance is preferable as illustrated in FIG. 12. In this case, it is more preferable that a center-to-center interval 31f of the two adjacent through-holes 31 in the width direction WD is shorter than a length 31x of each of the through-holes 31 in the width direction WD.

In general, especially when stretching stress is in a range of 4 to 12 N/35 mm in stretching the elastic film 30 four times in the width direction WD, in a state in which the non-stretchable region 70 is stretched to the elastic limit in the width direction WD, the center-to-center interval 31e of the two adjacent through-holes 31 in the front-back direction LD is preferably in a range of 0.4 to 2.7 mm, and the length 31y of each of the through-holes 31 in the front-back direction LD is preferably in a range of 0.5 to 3.0 mm, particularly in a range of 0.7 to 1.1 mm. In addition, the center-to-center interval 31*f* of the two adjacent through-holes 31 in the width direction WD is preferably 0.5 to 2 times, particularly 1 to 1.2 times the length 31*y* of the through-holes 31 in the front-back direction LD, and the length 31*x* of each of the through-holes 31 in the width direction WD is preferably 1.1 to 1.8 times, particularly 1.1 to 1.4 times the center interval 31*f* of the through-holes 31 in the width direction WD. In a state in which the non-stretchable region 70 is stretched to an elastic limit in the width direction WD (in other words, in a state in which the first sheet layer 20A and the second sheet layer 20B are completely spread), the center-to-center interval 31*f* of the two adjacent through-holes 31 in the width direction WD is equal to a center-to-center interval 40*f* of the two adjacent sheet bonded portions 40 in the width direction WD, the center-to-center interval 31*e* of the two adjacent through-holes 31 in the front-back direction LD is equal to a center-to-center interval 40*e* of the two adjacent sheet bonded portions 40 in the front-back direction LD, and the length 31*y* of each of the through-holes 31 in the front-back direction LD is equal to the length 40*y* of each of the sheet bonded portions 40 in the front-back direction LD.

In a case in which neither the first sheet layer 20A nor the second sheet layer 20B is bonded to the elastic film 30 at least in a portion other than a portion between the first sheet layer 20A and the second sheet layer 20B in the sheet bonded portions 40 in the non-stretchable region 70, and the gaps, which are generated by the peripheral edge of each of the through-holes 31 of the elastic film 30 and each of the sheet bonded portions 40 separated from each other, are included at both sides of each of the sheet bonded portions 40 in the width direction WD in the natural length state, air permeability is imparted at all times due to the gaps even if the material of the elastic film 30 is a non-porous film or a non-porous sheet, and thus such a case is preferable. In the case of adopting a scheme of simultaneously forming the through-holes 31 and the sheet bonded portions 40 described above, this state is automatically obtained irrespective of a shape of the sheet bonded portions 40, etc.

The shape of each of the sheet bonded portions 40 and the through-holes 31 in the natural length state is not particularly restricted. However, it is desirable to have a small area from a viewpoint of flexibility, and it is desirable to have a shape which is long in the front-back direction LD to eliminate linear continuity in the width direction WD of the elastic film 30. Thus, it is preferable to adopt an ellipse which is long in the front-back direction LD, a rectangle (see FIG. 11), the rhombus (see FIG. 13(*b*)), the convex lens shape (see FIG. 13(*a*)), and the concave lens shape (see FIG. 14(*a*)). However, when corners are acute as in the rhombus, the elastic film 30 is easily fractured. In contrast, the convex lens shape is preferable since welding of the sheet bonded portions 40 is stabilized, and the concave lens shape is preferable in that an area may be further reduced.

It is possible to appropriately determine the area rate of the sheet bonded portions 40 and the area of each of the sheet bonded portions 40 in the non-stretchable region. However, in general, ranges below are preferable since the area of each of the sheet bonded portions 40 is small, the area rate of the sheet bonded portions 40 is low, and thus the non-stretchable region 70 is not hardened.

Area of each of sheet bonded portions 40: 0.10 to 0.75 mm$^2$ (particularly 0.10 to 0.35 mm$^2$)

Area rate of sheet bonded portions 40: 4 to 13% (particularly 5 to 10%)

As described above, the elongation at the elastic limit of the non-stretchable region 70 may be changed by the arrangement pattern of the through-holes 31, dimensions of each of the through-holes 31, and the center-to-center interval of the two adjacent through-holes 31. Therefore, although not illustrated, it is possible to make the elongation at the elastic limit different between a plurality of positions in the stretchable region 80 or a plurality of non-stretchable regions 70. For example, in a preferable mode, the elongation at the elastic limit in the non-stretchable region 70 of the front body F is set to be larger than the elongation at the elastic limit in the non-stretchable region 70 of the back body B.

Even though the non-stretchable region 70 has a section that linearly continues along the width direction WD similarly to the stretchable region, since the area rate of the sheet bonded portions in the non-stretchable region 70 is higher than that in the stretchable region, the elongation at the elastic limit is remarkably low in the non-stretchable region 70. Specifically, it is possible to adopt another mode for eliminating elasticity such as a mode in which the elongation at the elastic limit is 130% or less, a mode in which cutting is performed in the width direction WD at one position or a plurality of positions as in a conventional stretchable structure using a rubber thread, etc.

(With Regard to Prevention of Welding Defect in Ultrasonic Welding)

In a case of forming the elastic film stretchable structure 20X by the ultrasonic welding, to prevent a welding defect, it is desirable for the anvil roll 60 that in its region having the protrusions 60*a*, a range in the roll length direction QD facing at least one ultrasonic horn 61 has a portion in which the area rate of the protrusions 60*a* changes in the roll circumferential direction RD, and a difference between a maximum value and a minimum value in the change of the area rate of the protrusions 60*a* in the roll circumferential direction RD is set to 4.5% or less. The difference between the maximum value and the minimum value in the change of the area rate of the protrusions 60*a* in the roll circumferential direction RD of the anvil roll 60 is set to 4.5% or less in this way, which makes a difference in thermal expansion in the roll circumferential direction RD small during a long time operation. Thus, the lack of time to control the clearance of the ultrasonic horn 61 rarely occurs, and a welding defect is hardly caused.

In addition to or in place of making the change of the area rate of the protrusions 60*a* in the roll circumferential direction RD fall in within a predetermined range, it is desirable for the anvil roll 60 that in its region having the protrusions 60*a*, a site for welding performed by at least one ultrasonic horn 61 (in other words, a site in the roll length direction QD facing a tip surface of the ultrasonic horn 61) has a portion in which the area rate of the protrusions 60*a* changes in the roll length direction QD, and a difference between a maximum value and a minimum value in the change of the area rate of the protrusions 60*a* in the roll length direction QD is set to 1.5% or less. The difference between the maximum value and the minimum value in the change of the area rate of the protrusions 60*a* in the roll length direction QD of the anvil roll 60 is set to 1.5% or less in this way, which makes a difference in thermal expansion in the roll length direction QD small during a long time operation. Thus, a clearance between the ultrasonic horn 61 and the anvil roll 60 rarely becomes excessively large in a region in which thermal expansion is small in the CD, and a welding defect hardly occurs.

Figure 23:
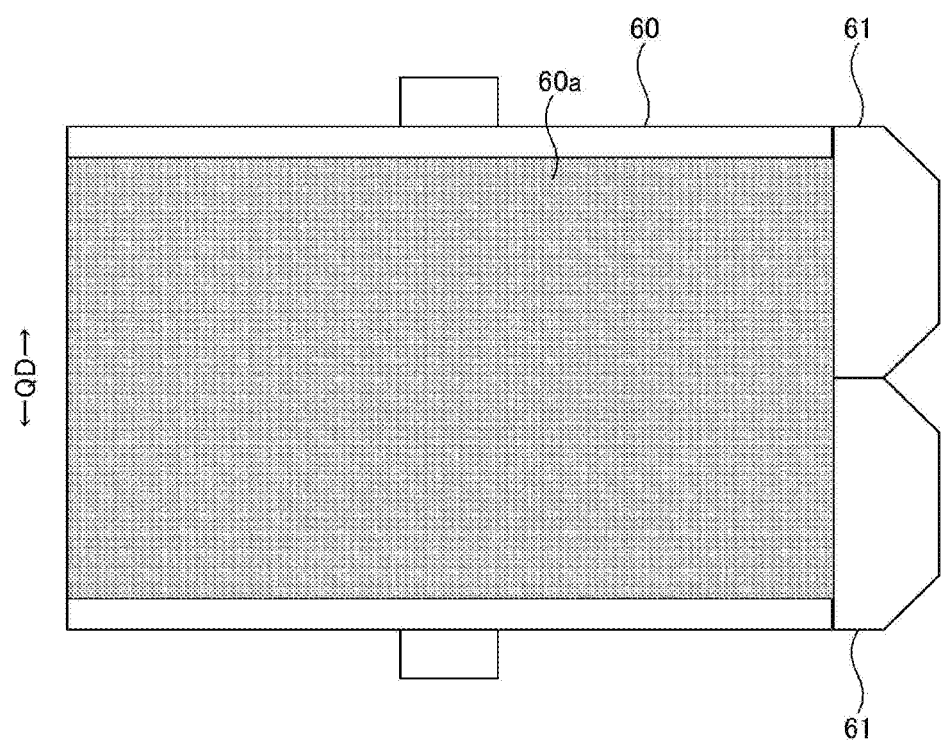
FIG. 23 is a plan view illustrating a positional relationship between the anvil roll and ultrasonic horns.

In ultrasonic welding, when a width of the ultrasonic horn 61 increases, a welding defect in the roll length direction QD described above is likely to occur. Thus, in a case in which ultrasonic welding is performed for a certain length or for longer than the certain length in the CD, it is desirable to perform a process by arranging a plurality of ultrasonic horns 61 for one anvil roll 60 as illustrated in FIG. 23. Further, in this case, even though the difference between the maximum value and the minimum value in the change of the area rate of the protrusions 60a may be set with respect to all protrusions 60a of one anvil roll 60, it is desirable that the difference between the maximum value and the minimum value in the change of the area rate of the protrusions 60a in the roll length direction QD is set to 1.5% or less for each site in which welding is performed by each ultrasonic horn 61.

Figure 22:
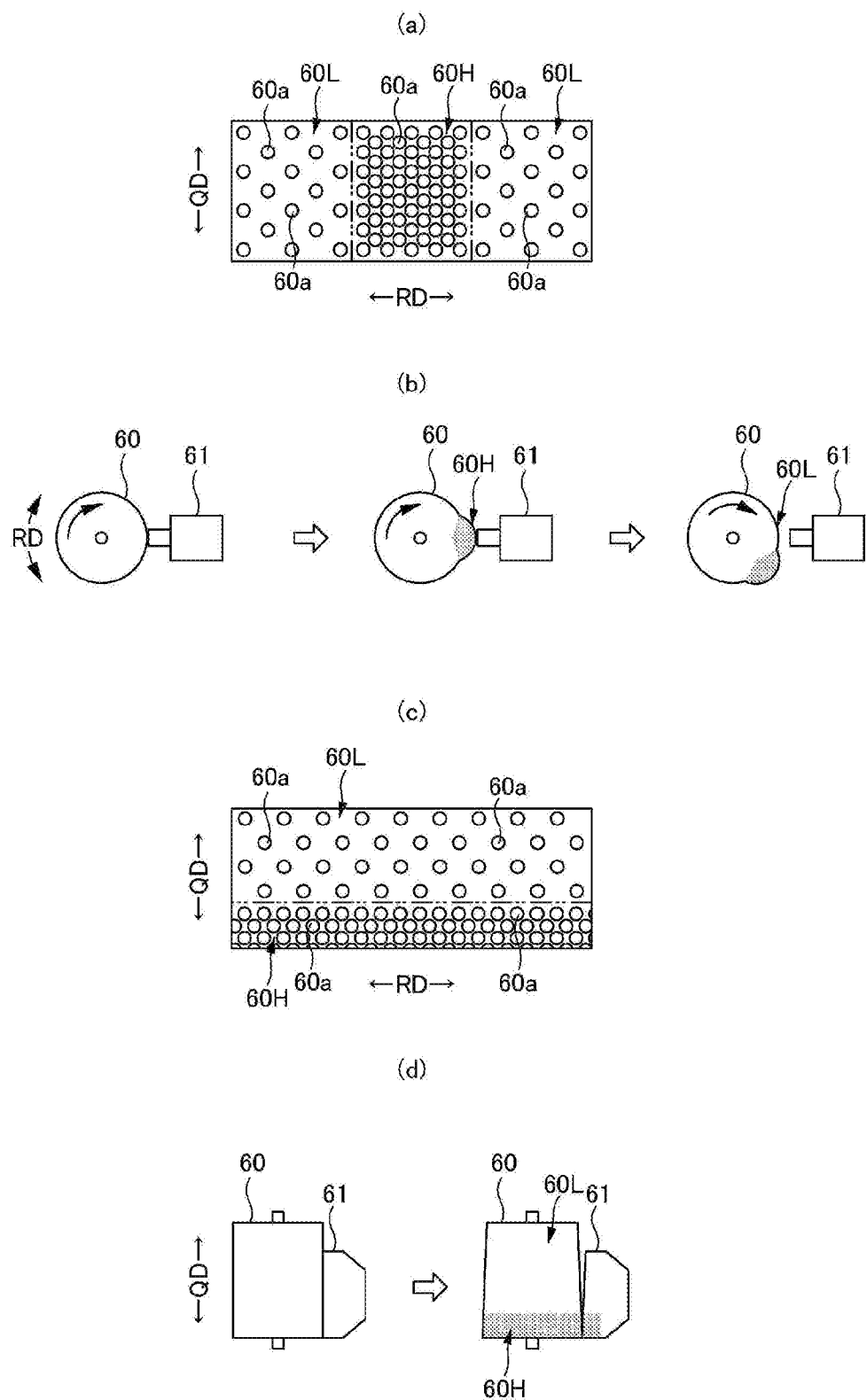
FIG. 22(a) is a development figure of regions of protrusions on an outer peripheral surface of an anvil roll.
FIG. 22(b) is an explanatory diagram for thermal expansion of an ultrasonic welding device.
FIG. 22(c) is a development figure of regions of protrusions on the outer peripheral surface of the anvil roll.
FIG. 22(d) is an explanatory diagram for thermal expansion of the ultrasonic welding device.
Figure 24:
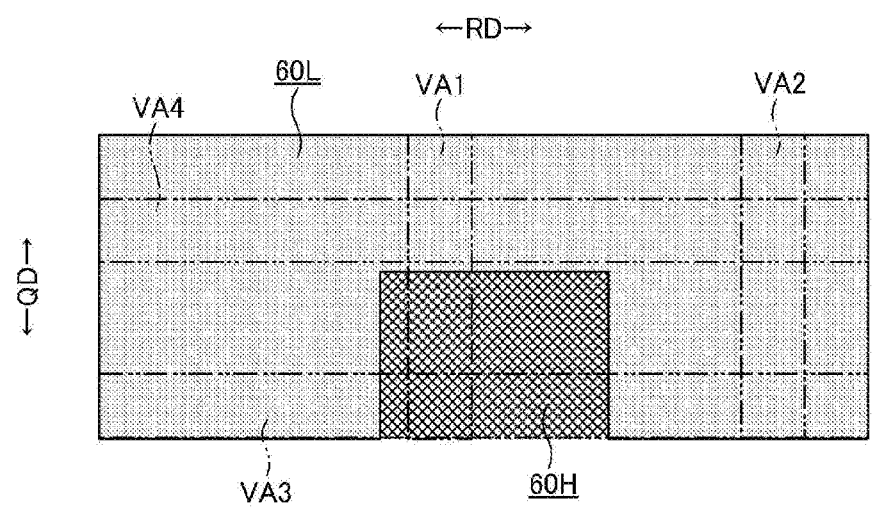
FIG. 24 is a development figure of the regions of the protrusions on a peripheral surface of the anvil roll.
Figure 24:
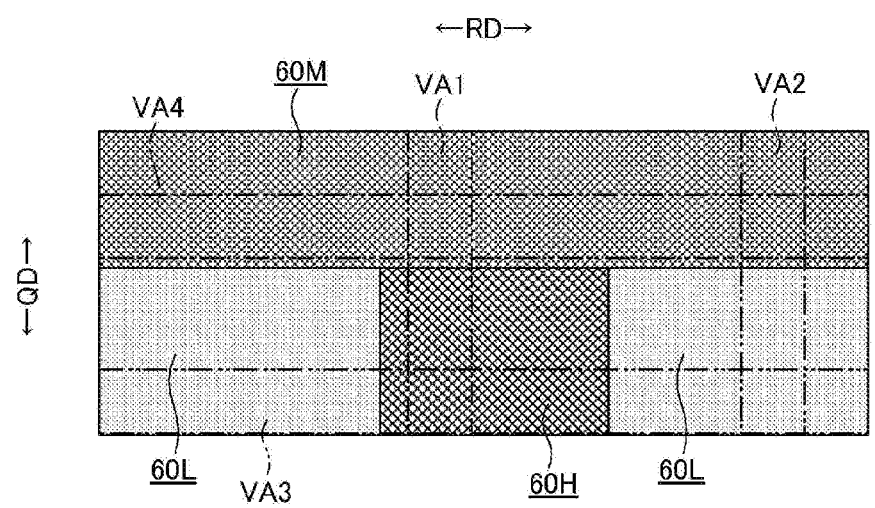

For example, when it is presumed that the whole pattern of the protrusions 60a of the anvil roll 60 illustrated in FIG. 24(a) corresponds to a site in which welding is performed by one ultrasonic horn 61, in this anvil roll 60, one side in the roll length direction QD corresponds to a pattern in which the low-area-rate-region 60L having the low area rate of the protrusions 60a continues in the circumferential direction, and the other side in the roll length direction QD corresponds to a mode in which the area rate is changed from the low-area-rate-region 60L having the low area rate of the protrusions 60a to the high-area-rate-region 60H having the high area rate of the protrusions 60a and then, reversely, from the high-area-rate-region 60H to the low-area-rate-region 60L. In addition, in apart of the range in the roll circumferential direction RD, there is a mode in which the area rate of the protrusions 60 a is changed also in the roll length direction QD. In this mode, both a difference in thermal expansion illustrated in FIGS. 22(a) and 22(b) and a difference in thermal expansion illustrated in FIGS. 22(c) and 22(d) are problematic, and there is concern about a welding defect depending on the area rate of the protrusions 60a. This arrangement presumes a pattern for manufacturing the elastic film stretchable structure 20X of the lower torso portion T illustrated in FIG. 2.

Figure 25:
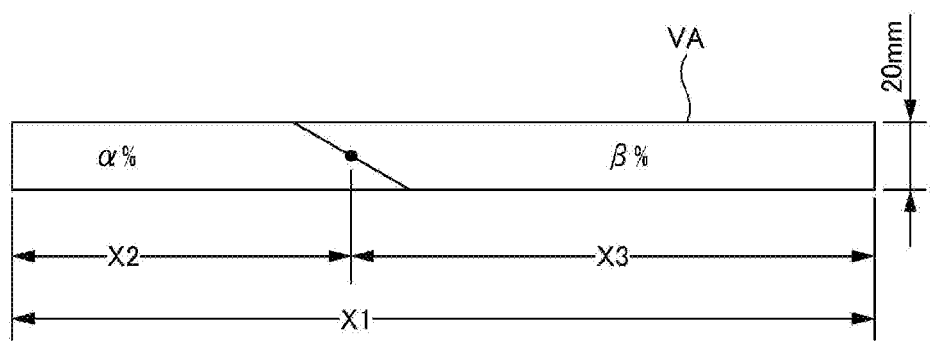
FIG. 25 is an explanatory diagram for a calculation method of an area rate.
Figure 25:
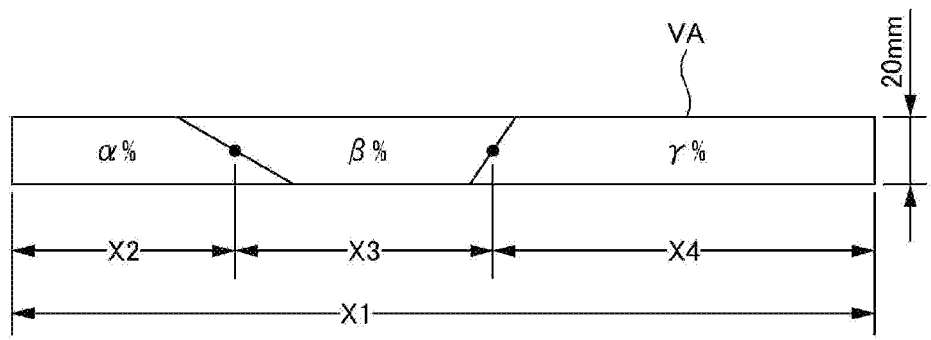

Here, a maximum value and a minimum value in a change of the area rate of the protrusions 60a in a specific direction (the roll circumferential direction RD or the roll length direction QD) refer to a maximum value and a minimum value of the area rate of the protrusions 60a obtained at each position in the specific direction in a virtual partition VA having a length in a direction orthogonal to the specific direction of 20 mm as illustrated in FIG. 25. As illustrated in FIG. 25, when a plurality of regions having respective different area rates of the protrusions 60a is present in the virtual partition VA, an area rate obtained by taking into account a proportion occupied by each region is regarded as the area rate of the virtual partition.

In more detail, as illustrated in FIG. 25(a), when two regions corresponding to a region having an area rate of 60% and a region having an area rate of 62% are included in the virtual partition VA, a length of the virtual partition VA in the specific direction is set to Xl, and lengths of the respective regions in the specific direction (lengths of center lines passing through a center in a direction orthogonal to the specific direction) are set to X2 and X3, an area rate Am of the virtual partition becomes $$Am=(\alpha \times (X2/X1))+(\beta \times (X3/X1)) \qquad (1)$$

In addition, as illustrated in FIG. 25(b), when three regions corresponding to a region having an area rate of α%, a region having an area rate of β%, and a region having an area rate of γ% (including a case of α=γ) are included in the virtual partition VA, the length of the virtual partition VA in the specific direction is set to X1, and lengths of the respective regions in the specific direction (lengths of center lines passing through centers in the direction orthogonal to the specific direction) are set to X2, X3, and X4, the area rate Am of the virtual partition becomes $$Am=(\alpha \times (X2/X1))+(\beta \times (X3/X1))+(\gamma \times (X4/X1)) \qquad (2)$$

Considering a case in which the area rate of the low-area-rate-region 60L is 3% and the area rate of the high-area-rate-region 60H is 6% in a pattern of the protrusions 60a of the anvil roll 60 illustrated in FIG. 24(a), a maximum value in the change of the area rate of the protrusions 60a in the roll circumferential direction RD is 4.5% obtained from Equation (1) in a virtual partition VA1, a minimum value thereof is 3% in a virtual partition VA2, and a different is 3%. In addition, a maximum value in the change of the area rate of the protrusions 60a in the roll length direction QD is 4% obtained from Equation (1) in a virtual partition VA3, a minimum value thereof is 3% in a virtual partition VA4, and a different is 1%. In other words, this example is a preferred example included in the scope of the invention.

Next, a considered case is that the whole pattern of the protrusions 60a of the anvil roll 60 illustrated in FIG. 24(b) corresponds to a site in which welding is performed by one ultrasonic horn 61. In this anvil roll 60, one side in the roll length direction QD corresponds to a pattern in which a medium-area-rate-region 60M having a medium area rate of the protrusions 60a continues in the circumferential direction, and the other side in the roll length direction QD corresponds to a mode in which the area rate is changed from the low-area-rate-region 60L having the lower area rate of the protrusions 60a than that of the medium-area-rate-region 60M to the high-area-rate-region 60H having a higher area rate of the protrusions 60a than that of the medium-area-rate-region 60M and then, reversely, from the high-area-rate-region 60H to the low-area-rate-region 60L. In this mode, both the difference in thermal expansion illustrated in FIGS. 22(a) and 22(b) and the difference in thermal expansion illustrated in FIGS. 22(c) and 22(d) are problematic, and there is concern about a welding defect caused depending on the area rate of the protrusions 60a.

Considering a case in which the area rate of the low-area-rate-region 60L is 3%, the area rate of the medium-area-rate-region 60M is 4%, and the area rate of the high-area-rate-region 60H is 6% in a pattern of the protrusions 60a of the anvil roll 60 illustrated in FIG. 24(b), a maximum value in the change of the area rate of the protrusions 60a in the roll circumferential direction RD is 5% obtained from Equation (1) applying to the virtual partition VA1, whereas a minimum value thereof is 3.5% obtained from Equation (1) applying to the virtual partition VA2, and a different is 1.5%. In addition, as for the change of the area rate of the protrusions 60a in the roll length direction QD, since there are only two patterns, the virtual partitions VA3 and VA4, both of which have the same area rate of 4% obtained by applying Equation (1), a maximum value and a minimum value are equally 4%, and a difference is 0%. In other words, this example is a preferred example included in the scope of the invention. In addition, as is understood from this example, the invention includes a case in which a maximum value and a minimum value in the change of the area rate of the protrusions 60a are equal to each other.

Meanwhile, in the elastic film stretchable structure 20X manufactured by ultrasonic welding described above, the sheet bonded portions 40 are formed so as to have substantially the same size and arrangement as those of protrusions of the anvil roll 60. Therefore, in a region having the elastic film stretchable structure 20X in the underpants-type disposable diaper described above, if a site ranging totally in the stretchable direction and at least partly in the orthogonal direction XD (front-back direction LD) has a portion in which the area rate of the sheet bonded portions 40 changes in the stretchable direction ED (width direction WD), satisfying at least one of two requirements: one requirement in which a difference between a maximum value and a minimum value in a change of an area rate of the sheet bonded portions 40 in the stretchable direction ED is 4.5% or less; and the other requirement in which a difference between a maximum value and a minimum value in a change of an area rate of the sheet bonded portions 40 in the orthogonal direction XD is 1.5% or less, such a site may be regarded to be particularly suitable for forming the elastic film stretchable structure 20X by using the ultrasonic welding. In addition, such an elastic film stretchable structure 20X has an improved uniformity in configuration at least in one of the stretchable direction ED and the orthogonal direction XD in the region having the elastic film stretchable structure 20X. Thus, more uniform texture, flexibility, elasticity, etc. can be attained. Here, it is desirable in the region having the elastic film stretchable structure 20X that a range in the orthogonal direction XD meeting the above-mentioned conditions is adjusted to a position and a width of the ultrasonic horn 61 at the time of manufacture. However, the range may be narrower or wider. In a normal case, the width of the ultrasonic horn 61 is desirably about 100 to 200 mm in view of efficiency and stability of ultrasonic welding. Thus, it is desirable that the region having the elastic film stretchable structure 20X is partitioned at intervals of 100 to 200 mm in the orthogonal direction XD, and the difference between the maximum value and the minimum value of the area rate mentioned above is satisfied in each of partitioned regions. In addition, a case is possible in which the above-mentioned conditions are met in an entire part in which the elastic film 30 continues.

(Welding Quality Confirmation Test)

Figure 26:
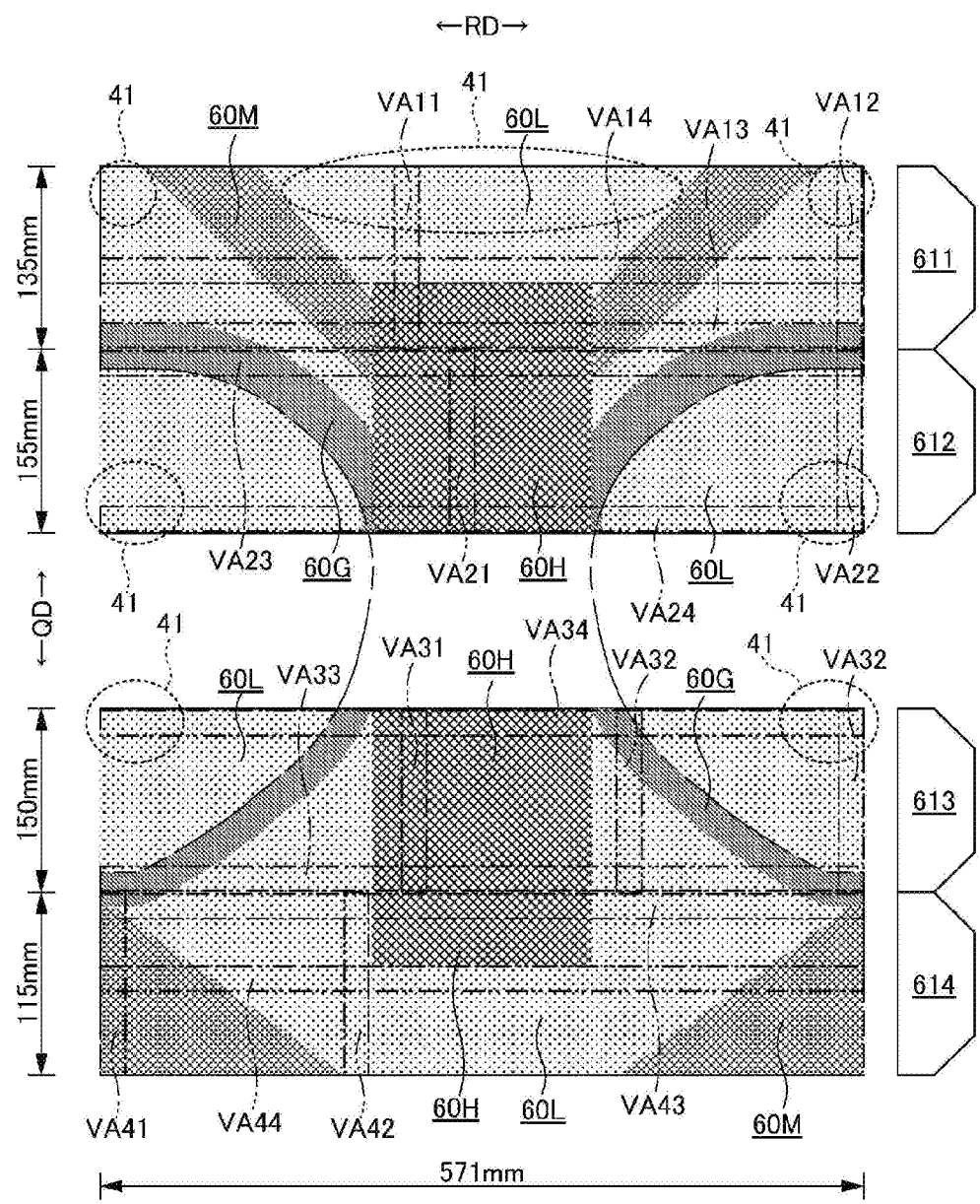
FIG. 26 is a development figure of the regions of the protrusions on the peripheral surface of the anvil roll in an example.

Using the anvil roll 60 having a pattern of the protrusions 60a (presuming the absorbent article illustrated in FIG. 15) illustrated in FIG. 26 with the ultrasonic welding device illustrated in FIG. 20, ultrasonic welding was performed for the first sheet layer 20A, the second sheet layer 20B and the elastic film 30 interposed therebetween, and for the welded substance, the presence or absence of an unwelded portion was visually confirmed after continuous operation for 20 minutes. Test conditions are as follows.

In the processing facilities illustrated in FIG. 20, as illustrated in FIG. 26, for one anvil roll 60, four ultrasonic horns 611 to 614 in total, two ultrasonic horns on each of the front body F side and the back body B side, were arranged in the roll length direction QD of the anvil roll 60, and ultrasonic welding was performed at one time. In the ultrasonic welding device, a material of the anvil roll 60 is tool steel having a thermal expansion coefficient of about 12 to 14 ($\times 10^{-6}$/° C.), and a material of the ultrasonic horn 61 is low expansion metal having a thermal expansion coefficient of about 8 to 10 ($\times 10^{-6}$/° C.).

First sheet layer 20A and second sheet layer 20B: spunbond nonwoven fabric having a basis weight of 17 g/m² made of PE/PP conjugate fiber (core: polypropylene (melting point 165° C.), sheath: polyethylene (melting point 130° C.)).

Elastic film 30: basis weight 30 g/m², thickness: 35 μm, melting point: 110 to 120° C., stretch rate in MD during welding: 350%.

Dimension in roll length direction QD of region corresponding to each of ultrasonic horns 611 to 614 in anvil roll 60: see FIG. 26.

Dimension in roll circumferential direction RD of one diaper in anvil roll 60: see FIG. 26.

First-high-area-rate-region 60H for forming non-stretchable region 70 (ventral side)
　Area of protrusion 60a: 0.14 mm²
　Area rate of protrusions 60a: 10.0%

First-high-area-rate-region 60H for forming non-stretchable region 70 (dorsal side)
　Area of protrusion 60a: 0.2 mm²
　Area rate of protrusions 60a: 10.0%

Low-area-rate-region 60L for forming stretchable region 80
　Area of protrusion 60a: 0.14 mm²
　Area rate of protrusions 60a: 1.8%

Medium-area-rate-regions 60M for forming oblique direction regions 81 and ilium facing regions 83
　Area of protrusion 60a: 0.64 mm²
　Area rate of protrusions 60a: 5.9%

Second-high-area-rate-regions 60G for forming edge portion regions 82 of leg openings
　Area of protrusion 60a: 0.64 mm²
　Area rate of protrusions 60a: 9.4%

Hereinafter, results of the test will be described in order. First, in a region corresponding to the first ultrasonic horn 611 in the anvil roll 60, a maximum value in the change of the area rate of the protrusions 60a in the roll circumferential direction RD was obtained at a virtual partition VA11 as 5.7% by a formula (1.8%×0.52)+(10%×0.48), a minimum value of the same was obtained at a virtual partition VA12 as 3.4% by a formula (1.8%×0.79)+(9.4%×0.21), and a difference therebetween was 2.3%. In addition, as for the change of the area rate of the protrusions 60a in the roll length direction QD, a maximum value was obtained at a virtual partition VA13 as 7.9% by a formula (1.8%×0.14)+(5.9%×0.20)+(9.4%×0.38)+(10%×0.29), a minimum value was obtained at a virtual partition VA14 as 3.2% by a formula (1.8%×0.65)+(5.9%×0.35), and a difference therebetween was 4.7%. Further, as a result of confirming a welding defect after continuous operation for 20 minutes, unwelded parts 41 were confirmed at three places in the roll circumferential direction RD on the virtual partition VA14 side.

Next, in a region corresponding to the second ultrasonic horn 612 in the anvil roll 60, a maximum value in the change of the area rate of the protrusions 60a in the roll circumferential direction RD was obtained at a virtual partition VA21 including only a region in which the area rate of the protrusions 60a as 10%, a minimum value of the same was obtained at a virtual partition VA22 as 2.1% by a formula (1.8%×0.96)+(9.4%×0.04), and a difference therebetween was 7.9%. In addition, as for the change of the area rate of the protrusions 60a in the roll length direction QD, a maximum value was obtained at a virtual partition VA23 as 6.7% by a formula (1.8%×0.34)+(5.9%×0.09)+(9.4%×0.27)+(10%×0.30), a minimum value was obtained at a virtual partition VA24 as 4.6% by a formula (1.8%×0.65)+(9.4%×0.05)+(10%×0.30), and a difference therebetween was 2.1%. Further, as a result of confirming a welding defect after continuous operation for 20 minutes, the unwelded parts 41 were confirmed at two places in the roll circumferential direction RD on the virtual partition VA24 side.

Next, in a region corresponding to the third ultrasonic horn 614 in the anvil roll 60, a maximum value in the change of the area rate of the protrusions 60a in the roll circumferential direction RD was obtained at a virtual partition VA31 including only a region in which the area rate of the protrusions 60a as 10%, a minimum value of the same was obtained at a virtual partition VA32 as 3.1% by a formula (1.8%×0.83)+(9.4%×0.17), and a difference therebetween was 6.9%. In addition, as for the change of the area rate of the protrusions 60a in the roll length direction QD, a maximum value was obtained at a virtual partition VA33 as 6.1% by a formula (1.8%×0.57)+(9.4%×0.13)+(10%×0.30), a minimum value was obtained at a virtual partition VA34 as 5.2% by a formula (1.8%×0.57)+(9.4%×0.13)+(10%×0.30), and a difference therebetween was 0.9%. Further, as a result of confirming a welding defect after continuous operation for 20 minutes, the unwelded parts 41 were confirmed at two places in the roll circumferential direction RD on the virtual partition VA34 side.

Next, in a region corresponding to the fourth ultrasonic horn 61 in the anvil roll 60, a maximum value in the change of the area rate of the protrusions 60a in the roll circumferential direction RD was obtained at a virtual partition VA41 as 6.3% by a formula (5.9%×0.90)+(9.4%×0.10), a minimum value was obtained at a virtual partition VA42 including only a region in which the area rate of the protrusions 60a as 1.8%, and a difference therebetween was 4.5%. In addition, as for the change of the area rate of the protrusions 60a in the roll length direction QD, a maximum value was obtained at a virtual partition VA43 as 4.8% by a formula (1.8%×0.58)+(5.9%×0.11)+(10%×0.30), a minimum value was obtained at a virtual partition VA44 as 3.3% by a formula (1.8%×0.63)+(5.9%×0.37), and a difference therebetween was 1.5%. Further, as a result of confirming a welding defect after continuous operation for 20 minutes, an unwelded part was not confirmed in the entire region.

The above results are summarized as follows. From this result, in the anvil roll 60, it was found that in a site in which welding is performed by at least one ultrasonic horn 61, when the difference between the maximum value and the minimum value in the change of the area rate of the protrusions 60a in the roll circumferential direction RD is 4.5% or less, a welding defect due to a difference in coefficient of thermal expansion in the roll circumferential direction RD does not occur. In addition, it was found that when the difference between the maximum value and the minimum value in the change of the area rate of the protrusions 60a in the roll length direction QD is 1.5% or less, a welding defect due to a difference in coefficient of thermal expansion in the roll length direction QD does not occur.

TABLE 1

| Roll circumferential direction | | Roll length direction | |
| --- | --- | --- | --- |
| Difference between maximum value and minimum value of area rate (%) | Presence or absence of non-welding | Difference between maximum value and minimum value of area rate (%) | Presence or absence of non-welding |
| 2.3 | Absent | 4.7 | Present |
| 7.9 | Present | 2.1 | Present |
| 6.9 | Present | 0.9 | Absent |
| 4.5 | Absent | 1.5 | Absent |

<Description of Terms in Specification>

The terms used in the specification have the following meanings unless otherwise stated.

The "MD" and the "CD" in the manufacturing method refer to a flow direction (MD) in a manufacturing facilities and a lateral direction (CD) orthogonal thereto, and either one of which is the front-back direction of the product and the other one of which is the width direction of the product. In addition, the MD of the nonwoven fabric represents a direction of fiber orientation of the nonwoven fabric. The fiber orientation refers to a direction along which a fiber of the nonwoven fabric extends. For example, it is possible to perform determination by a measuring method in accordance with a fiber orientation test method based on zero-span tensile strength of a TAPPI T 481 or a simplified testing method that determines the direction of the fiber orientation from a ratio of the tensile strengths of the front-back direction to the width direction.

The "front body" and the "back body" refer to front and back portions using the center of the underpants-type disposable diaper in the front-back direction as a boundary. In addition, the crotch portion refers to a front-back direction range including the center of the underpants-type disposable diaper in the front-back direction, and refers to a front-back direction range of a portion having a narrowing part when the absorber has the narrowing part.

The "elongation at the elastic limit" refers to an elongation at an elastic limit in the stretchable direction (in other words, a state in which the first sheet layer and the second sheet layer are completely spread), and expresses a length at the time of the elastic limit as a percentage when the natural length is set to 100%.

The "area rate" refers to a rate of a target portion to a unit area, and expresses the rate as a percentage by dividing a total area of the target portions (for example, the sheet bonded portions 40, the openings of the through-holes 31, and the vent hole) in a target region (for example, the stretchable region 80, the non-stretchable region 70, a main stretchable portion, and a damping elastic portion) by an area of the target region. Particularly, an "area rate" in a region having a stretchable structure refers to an area rate in a state of being stretched in the stretchable direction to the elastic limit. In a mode in which a large number of target portions are provided at intervals, it is desirable to obtain the area rate by using the target region of a size including ten or more target portions are included.

The "stretch rate" represents a value relative to the natural length (100%)

The "basis weight" is determined as follows: After the sample or test piece is preliminarily dried, it is allowed to stand in a test room or apparatus under normal conditions (the test location is at a temperature: 20±5° C., relative humidity: 65% or less) until the constant mass. The preliminary drying is to make the sample or test piece be constant mass in an environment within a relative humidity of 10 to 25% and at a temperature not exceeding 50° C. The fibers of an official moisture regain of 0.0% does not need preliminary drying. A cut sample with a size of 200 mm by 250 mm (±2 mm) is cut from the test piece in the constant mass, with a cutting template (200 mm by 250 mm, ±2 mm). The sample is weighed and the weight is multiplied by 20 into the weight per square meter. The resulting value is defined as the basis weight.

The "thickness" of the absorber is measured using a thickness measurement apparatus of OZAKI MGF Co., Ltd. (PEACOCK, Dial Thickness Gauge Large Type, Model J-B (Measurement Range 0 to 35 mm) or Model K-4 (Measurement Range 0 to 50 mm)) by horizontally disposing a sample and the thickness measurement apparatus.

A "thickness" other than the above-described thickness is automatically determined with an automatic thickness gauge (KES-G5 handy compression measurement program) under the conditions of a load of 10 gf/cm² and a pressurization area of 2 cm².

The "tensile strength" and the "tensile elongation (elongation at break)" are measured at an initial chuck interval of 50 mm and a speed of testing of 300 mm/min with a tensile tester (for example, AUTOGRAPHAGS-G100N available from SHIMADZU) in accordance with JIS K7127:1999 "Plastics—Determination of tensile properties", except that the test piece is a rectangle with a width of 35 mm and a length of 80 mm.

The "stretching stress" indicates the tensile stress (N/35 mm) when the sample is stretched in an elastic region that is measured by a tensile test at an initial chuck interval (distance between marked lines) of 50 mm and a speed of testing of 300 mm/min in accordance with JIS K7127:1999 "Plastic—Determination of tensile properties", and an extent of stretching may be appropriately determined depending on the test object. A test piece is preferably formed in a rectangular shape having a width of 35 mm and a length of 80 mm or more. If a test piece with a width of 35 mm cannot be prepared, the test piece with a maximum possible width is prepared and the observed value is converted into a value at a width of 35 mm. Even if a sufficiently large test piece cannot be prepared from a target region with a small area, small test pieces can also be used for comparison of the stretching stress. For example, AOUTGRAPHAGS-G100N manufactured by SHIMADZU may be used as a tensile tester.

The "spread state" refers to a flatly unfolded state without contraction or slack.

Unless otherwise specified, dimensions of each portion refer to dimensions in the spread state, not in the natural length state.

In the absence of description about an environmental condition in a test or measurement, the test or measurement is performed in a test room or apparatus under normal conditions (the test location is at a temperature 20±5° C., relative humidity 65% or less).

INDUSTRIAL APPLICABILITY

The invention is applicable to a lower torso portion or a fastening tape of a tape type disposable diaper in addition to an underpants-type disposable diaper, and is applicable to another stretchable portion of a three-dimensional gather, a flat gather, etc. widely used in all absorbent articles including another type of disposable diaper such as an underpants-type disposable diaper, a sanitary napkin, etc.

REFERENCE SIGNS LIST

B BACK BODY
F FRONT BODY
T LOWER TORSO PORTION
L INTERMEDIATE PORTION
LD FRONT-BACK DIRECTION
WD WIDTH DIRECTION
ED STRETCHABLE DIRECTION
XD ORTHOGONAL DIRECTION
RD ROLL CIRCUMFERENTIAL DIRECTION
QD ROLL LENGTH DIRECTION
10 INNER MEMBER
11 LIQUID PERVIOUS TOP SHEET
12 LIQUID IMPERVIOUS SHEET
13 ABSORBER
13N NARROWING PART
14 WRAPPING SHEET
15 GATHER NONWOVEN FABRIC
16 GATHER ELASTIC MEMBER
20 OUTER MEMBER
20A FIRST SHEET LAYER
20B SECOND SHEET LAYER
20C FOLDED PART
20X ELASTIC FILM STRETCHABLE STRUCTURE
21 SIDE SEAL PORTION
23 WAIST REGION
24 WAIST PORTION ELASTIC MEMBERS
25 CONTRACTION WRINKLE
29 LEG LINE
30 ELASTIC FILM
31 THROUGH-HOLE
40 SHEET BONDED PORTION
41 UNWELDED PART
70 NON-STRETCHABLE REGION
80 STRETCHABLE REGION
60 ANVIL ROLL
60a PROTRUSION
60L LOW AREA RATE REGION
60M MEDIUM AREA RATE REGION
60H HIGH AREA RATE REGION
61 ULTRASONIC HORN

The invention claimed is:

1. A method of forming an elastic film stretchable structure comprising:
    a supply step of interposing an elastic film between a first sheet layer and a second sheet layer in a stretched state in a machine direction (MD); and
    a bonding step of passing the first sheet layer, the second sheet layer, and the elastic film interposed therebetween in the stretched state, between an anvil roll having a plurality of protrusions arranged at intervals in a predetermined pattern on an outer peripheral surface, and one or more ultrasonic horns facing the outer peripheral surface of the anvil roll, and forming sheet bonded portions by welding the first sheet layer and the second sheet layer only at portions interposed between the plurality of protrusions and the one or more ultrasonic horns, wherein
    the anvil roll includes a region having the plurality of protrusions,
    the region includes at least one site in which welding is performed by at least one of the one or more ultrasonic horns,
    the at least one site has a portion in which an area rate of a subset of the plurality of protrusions changes in a roll circumferential direction, and a difference between a maximum value and a minimum value in a change of the area rate of the subset of the plurality of protrusions in the roll circumferential direction is 4.5% or less.

2. A method of forming an elastic film stretchable structure comprising:
    a supply step of interposing an elastic film between a first sheet layer and a second sheet layer in a stretched state in an MD; and
    a bonding step of passing the first sheet layer, the second sheet layer, and the elastic film interposed therebetween in the stretched state, between an anvil roll having a plurality of protrusions arranged at intervals in a predetermined pattern on an outer peripheral surface, and one or more ultrasonic horns facing the outer peripheral surface of the anvil roll, and forming sheet bonded portions by welding the first sheet layer and the second sheet layer only at portions interposed between the plurality of protrusions and the one or more ultrasonic horns, wherein the anvil roll includes a region having the plurality of protrusions, the region includes at least one site in which welding is performed by at least one of the one or more ultrasonic horns, the at least one site has a portion in which an area rate of a subset of the plurality of protrusions changes in a roll length direction, and a difference between a maximum value and a minimum value in a change of the area rate of the subset of the plurality of protrusions in the roll length direction is 1.5% or less.

3. A method of forming an elastic film stretchable structure comprising:

a supply step of interposing an elastic film between a first sheet layer and a second sheet layer in a stretched state in an MD; and a bonding step of passing the first sheet layer, the second sheet layer, and the elastic film interposed therebetween in the stretched state, between an anvil roll having a plurality of protrusions arranged at intervals in a predetermined pattern on an outer peripheral surface, and one or more ultrasonic horns facing the outer peripheral surface of the anvil roll, and forming sheet bonded portions by welding the first sheet layer and the second sheet layer only at portions interposed between the plurality of protrusions and the one or more ultrasonic horns, wherein the anvil roll includes a region having the plurality of protrusions, the region includes at least one site in which welding is performed by at least one of the one or more ultrasonic horns, the at least one site has a portion in which an area rate of a subset of the plurality of protrusions changes in a roll circumferential direction and a roll length direction, a difference between a maximum value and a minimum value in a change of the area rate of the subset of the plurality of protrusions in the roll circumferential direction is 4.5% or less, and a difference between a maximum value and a minimum value in a change of the area rate of the subset of the plurality of protrusions in the roll length direction is 1.5% or less.

4. The method of forming an elastic film stretchable structure according to claim 1, wherein the one or more ultrasonic horns comprises a plurality of ultrasonic horns, in the bonding step, the plurality of ultrasonic horns is arranged in a roll length direction to face the region, and the welding is performed between the anvil roll and the plurality of ultrasonic horns, and the region includes a plurality of sites in which the welding is performed by each of the plurality of ultrasonic horns, and each of the plurality of sites has a respective portion in which an area rate of a respective subset of the plurality of protrusions changes in the roll length direction, and a difference between a maximum value and a minimum value in a change of the area rate of the respective subset of the plurality of protrusions in the roll length direction is 1.5% or less.

5. The method of forming an elastic film stretchable structure according to claim 1, wherein a melting point of the first sheet layer and the second sheet layer is 85 to 190° C., a melting point of the elastic film is 80 to 145° C., and a difference between the melting point of the first sheet layer and the second sheet layer and the melting point of the elastic film is 60 to 80° C.

6. The method of forming an elastic film stretchable structure according claim 2, wherein the one or more ultrasonic horns comprises a plurality of ultrasonic horns, in the bonding step, the plurality of ultrasonic horns is arranged in a roll length direction to face the region, and the welding is performed between the anvil roll and the plurality of ultrasonic horns, and the region includes a plurality of sites in which the welding is performed by each of the plurality of ultrasonic horns, and each of the plurality of sites has a respective portion in which an area rate of a respective subset of the plurality of protrusions changes in the roll length direction, and a difference between a maximum value and a minimum value in a change of the area rate of the respective subset of the plurality of protrusions in the roll length direction is 1.5% or less.

7. The method of forming an elastic film stretchable structure according claim 3, wherein the one or more ultrasonic horns comprises a plurality of ultrasonic horns, in the bonding step, the plurality of ultrasonic horns is arranged in a roll length direction to face the region, and the welding is performed between the anvil roll and the plurality of ultrasonic horns, and the region includes a plurality of sites in which the welding is performed by each of the plurality of ultrasonic horns, and each of the plurality of sites has a respective portion in which an area rate of a respective subset of the plurality of protrusions changes in the roll length direction, and a difference between a maximum value and a minimum value in a change of the area rate of the respective subset of the plurality of protrusions in the roll length direction is 1.5% or less.

8. The method of forming an elastic film stretchable structure according to claim 2, wherein a melting point of the first sheet layer and the second sheet layer is 85 to 190° C., a melting point of the elastic film is 80 to 145° C., and a difference between the melting point of the first sheet layer and the second sheet layer and the melting point of the elastic film is 60 to 80° C.

9. The method of forming an elastic film stretchable structure according to claim 3, wherein a melting point of the first sheet layer and the second sheet layer is 85 to 190° C., a melting point of the elastic film is 80 to 145° C., and a difference between the melting point of the first sheet layer and the second sheet layer and the melting point of the elastic film is 60 to 80° C.

10. The method of forming an elastic film stretchable structure according to claim 4, wherein a melting point of the first sheet layer and the second sheet layer is 85 to 190° C., a melting point of the elastic film is 80 to 145° C., and a difference between the melting point of the first sheet layer and the second sheet layer and the melting point of the elastic film is 60 to 80° C.

* * * * *